(12) United States Patent
Liu et al.

(10) Patent No.: US 9,421,369 B2
(45) Date of Patent: Aug. 23, 2016

(54) CIRCUIT ARCHITECTURE FOR HIGH CHANNEL COUNT HIGH-VOLTAGE NEURAL STIMULATOR

(71) Applicant: THE REGENTS OF THE UNIVERSITY OF CALIFORNIA, Oakland, CA (US)

(72) Inventors: Wentai Liu, Los Angeles, CA (US); Kuanfu Chen, Los Angeles, CA (US); Yi-Kai Lo, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/823,869

(22) Filed: Aug. 11, 2015

(65) Prior Publication Data

US 2016/0038739 A1    Feb. 11, 2016

Related U.S. Application Data

(63) Continuation of application No. PCT/US2014/015584, filed on Feb. 10, 2014.

(60) Provisional application No. 61/763,883, filed on Feb. 12, 2013.

(51) Int. Cl.
*A61N 1/36* (2006.01)
*A61N 1/372* (2006.01)
*A61N 1/378* (2006.01)
*A61N 1/05* (2006.01)

(52) U.S. Cl.
CPC ........ *A61N 1/36046* (2013.01); *A61N 1/36067* (2013.01); *A61N 1/36082* (2013.01); *A61N 1/36153* (2013.01); *A61N 1/3787* (2013.01); *A61N 1/37223* (2013.01); *A61N 1/0543* (2013.01)

(58) Field of Classification Search
None
See application file for complete search history.

(56) References Cited

U.S. PATENT DOCUMENTS

| | | |
|---|---|---|
| 2002/0091421 A1 | 7/2002 | Greenberg et al. |
| 2006/0241725 A1 | 10/2006 | Libbus et al. |
| 2008/0140154 A1 | 6/2008 | Loeb et al. |
| 2010/0042170 A1 | 2/2010 | Shuros et al. |
| 2011/0190849 A1 | 8/2011 | Faltys et al. |

OTHER PUBLICATIONS

Korean Intellectual Property Office, International Search Report and Written Opinion, PCT International Application No. PCT/US2014/015584, May 2, 2014, pp. 1-10, and claims searched, pp. 11-17.

*Primary Examiner* — Brian T Gedeon
(74) *Attorney, Agent, or Firm* — O'Banion & Ritchey LLP; John P. O'Banion

(57) ABSTRACT

A high channel count high-voltage neural stimulator provides an external circuit which communicates power and data to a neural stimulator implant circuit. Data from the external device, such as image data from a camera in an epiretinal application, are communicated to the implant. Multiple pixels circuits, within each implant demultiplex the digital signals, then output separate nerve stimulator outputs from multiple outputs, each configured for connection to a nerve, by sharing a single level conversion driver circuit. In at least one example, the implant circuits can be clustered in a master-slave configuration to increase the number of available neural stimulation outputs.

26 Claims, 20 Drawing Sheets

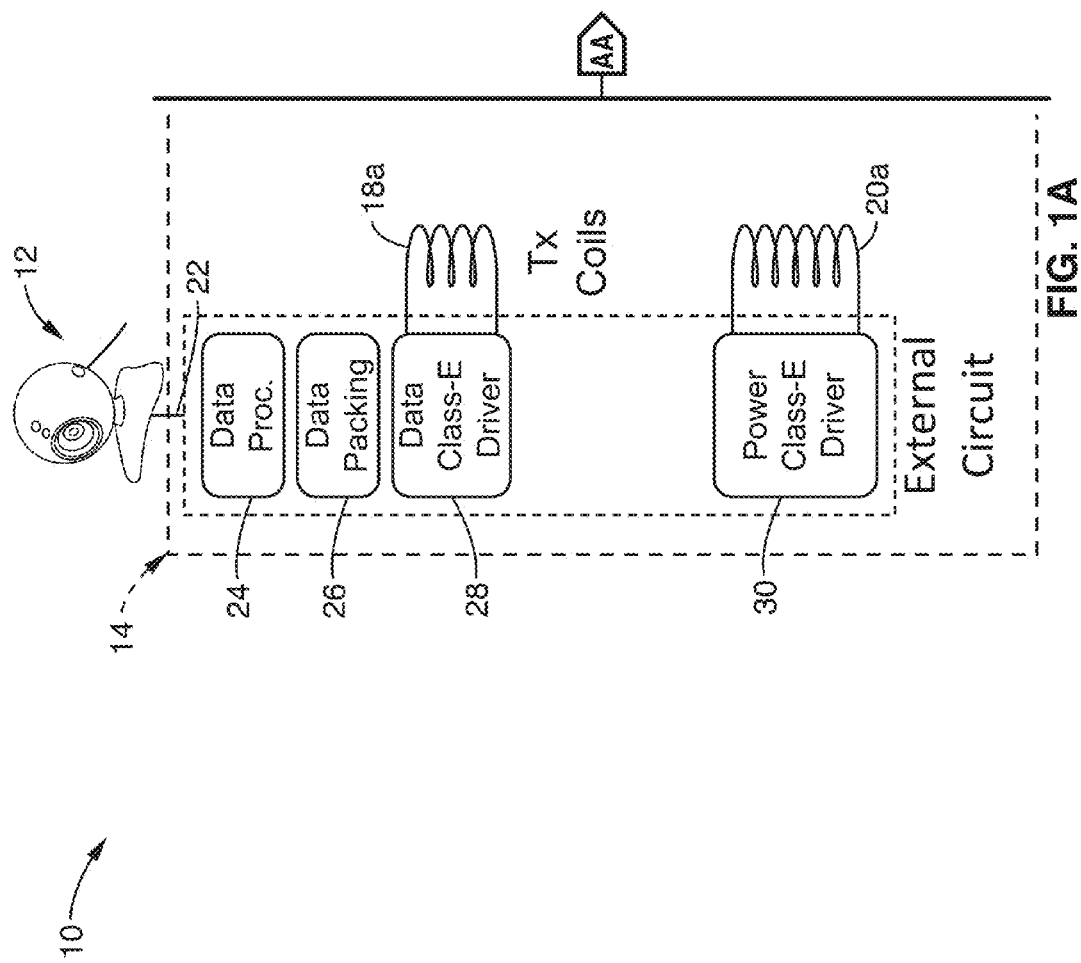

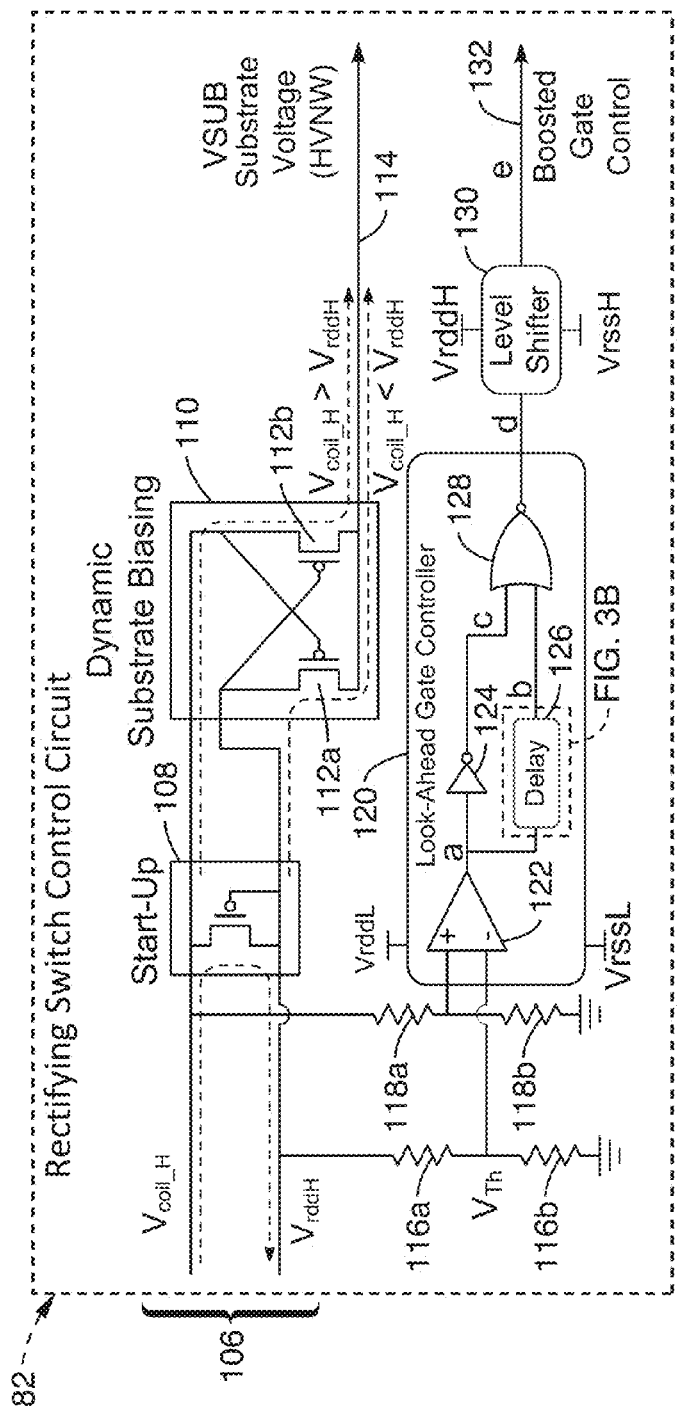
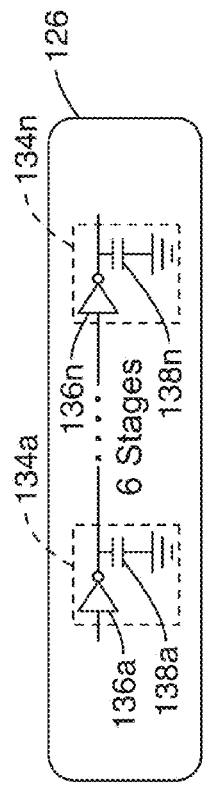
FIG. 3A
FIG. 3B

CIRCUIT ARCHITECTURE FOR HIGH CHANNEL COUNT HIGH-VOLTAGE NEURAL STIMULATOR

CROSS-REFERENCE TO RELATED APPLICATIONS

This application is a 35 U.S.C. §111(a) continuation of PCT international application number PCT/US2014/015584 filed on Feb. 10, 2014, incorporated herein by reference in its entirety, which claims priority to, and the benefit of, U.S. provisional patent application Ser. No. 61/763,883 filed on Feb. 12, 2013, incorporated herein by reference in its entirety. Priority is claimed to each of the foregoing applications.

The above-referenced PCT international application was published as PCT International Publication No. WO 2014/015584 on Aug. 12, 2014, which publication is incorporated herein by reference in its entirety.

STATEMENT REGARDING FEDERALLY SPONSORED RESEARCH OR DEVELOPMENT

This invention was made with Government support under 0310723 awarded by the National Science Foundation. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to biomedical stimulation implants, and more particularly to a high channel count high-voltage stimulator utilizing an electrical charge cancellation method.

2. Description of Related Art

Implants which provide high-voltage stimulation are being increasingly utilized for relieving a wide variety of medical conditions. Several high-voltage stimulator integrated circuits (ICs) have been reported in the past few years. Some of these stimulators reported in the literature provide multiple channel operation (e.g., 1024, 1600 channels), however, each have significant drawbacks for practical use, such as a large size per channel, requiring external diodes, limited output voltage compliance, requiring external power receiver circuit, and so forth.

Accordingly, a need exists for a high channel count high-voltage medical stimulator device which has a small circuit size per channel and overcomes the drawbacks of previous solutions.

BRIEF SUMMARY OF THE INVENTION

The inventive high-voltage (e.g., ±10V) stimulator circuit provides a fully integrated high-voltage high-channel-count stimulator for medical implants. The device has a small per-channel area and requires only a small number (e.g., five) off-chip components, which greatly simplifies the system packaging process. In one embodiment a 4096 channel high-voltage stimulator requires a circuit area of only 37.6 mm$^2$. The device is particularly well-suited for space-restricted medical implants, such as retinal prostheses, cochlear implants, and spinal (or other neural pathway) implants. It will be appreciated that many applications require a high count stimulation, with at least many (multiple) hundreds of stimulator outputs, with preferably over a thousand stimulators, and more preferably over four thousand stimulators. The circuit also incorporates an electrical charge cancellation scheme that can effectively remove residual charge from a stimulator electrode by precisely controlling either the width of either the anodic or cathodic current in a bi-phasic stimulus pattern.

The device provides a number of benefits for use in various medical implant applications. In addition, a chip clustering mechanism is utilized for increasing the total number of stimulation channels, while still providing independent control within each chip in the cluster. In at least one embodiment, an on-chip rectifier (e.g., quad-voltage on-chip rectifier) is integrated to eliminate the necessity of off-chip diodes. Techniques are employed to minimize circuit area, including "circuit-under-pad" and use of a globally-controlled demultiplexor (demux). Critical input/output (I/O) pads are duplicated, thus making the circuit more adaptive to various chip packaging methods. An electrical charge cancellation method is utilized that can eliminate residual charge for different sink/source mismatches, different electrodes, and variable stimulation amplitudes.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1A and FIG. 1B are a block diagram of a high channel count high-voltage stimulator circuit according to an embodiment of the present invention, shown implementing an epiretinal prosthesis system.

FIG. 3A and FIG. 3B are schematics of a rectifying switch control circuit for use in the high-voltage stimulator circuit according to an embodiment of the present invention.

DETAILED DESCRIPTION OF THE INVENTION

The present circuit for high channel count high-voltage (HV) stimulation, can simplify the implementation of a number of implant devices (e.g., retinal, spinal, cochlear), the following being described by way of example, and not limitation.

Retinal implants elicit light perception for persons blinded by photoreceptor loss. Although commercialized 60-channel retinal prostheses units allow patients to perform simple tasks, several hundred to a thousand or so electrodes are required to provide for facial recognition and reading tasks. This high channel count of stimulators poses a significant challenge in the design of next-generation retinal stimulators.

Aside from the higher power/data demand of a high channel count, the electrode impedance is also increased. Placing 1000 epiretinal electrodes in the 5 mm diameter macula region reduces the electrode size to less than 0.01 mm$^2$, leading to a 30 kΩ electrode-tissue impedance. It has been found that to elicit light perception of various brightness levels, the stimulators for epiretinal prostheses require an output compliance voltage of about ±10V, thus requiring area-consuming high-voltage (HV) transistors.

Devices exist which provide high count (e.g., 1600 channels) for sub-retinal stimulation utilizing low voltage compliance (e.g., ±2V) and requiring a separate chip for power telemetry. Utilizing that form of conventional design, a HV-compliant 1024-channel epiretinal prosthetic stimulator is estimated to occupy 64 mm$^2$ along with off-chip diodes for power rectification. It will be appreciated that for a space-restricted retinal implant, a small-sized fully integrated system-on-chip (SoC) embodiment utilizing a minimal number of off-chip components is preferable.

One embodiment of the present invention is an SoC implementation of a HV 1024-channel stimulator with fully integrated power and data telemetry. Prototypical implementations of the present invention have provided a chip (integrated circuit) with a die size of 37.6 mm$^2$, which is 42% smaller than a HV 1024-channel stimulator proposed in the literature, despite that the device proposed in the literature lacked fully integrated power and data telemetry. This SoC implementation, according to the invention, supports 100 mW total device power, including the power to operate the device and the power delivered to the tissue under stimulation. The inventive SoC implementation provides a quad-level rectifier and a 2 Mb/s data rate using a differential phase-shift keying (DPSK) demodulator. The stimulation array provides a ±10V compliance voltage and can be utilized to construct prosthetic devices having up to 1024 channel or prosthetic devices utilizing up to 4096 channels using chip clustering.

Figure 1B:
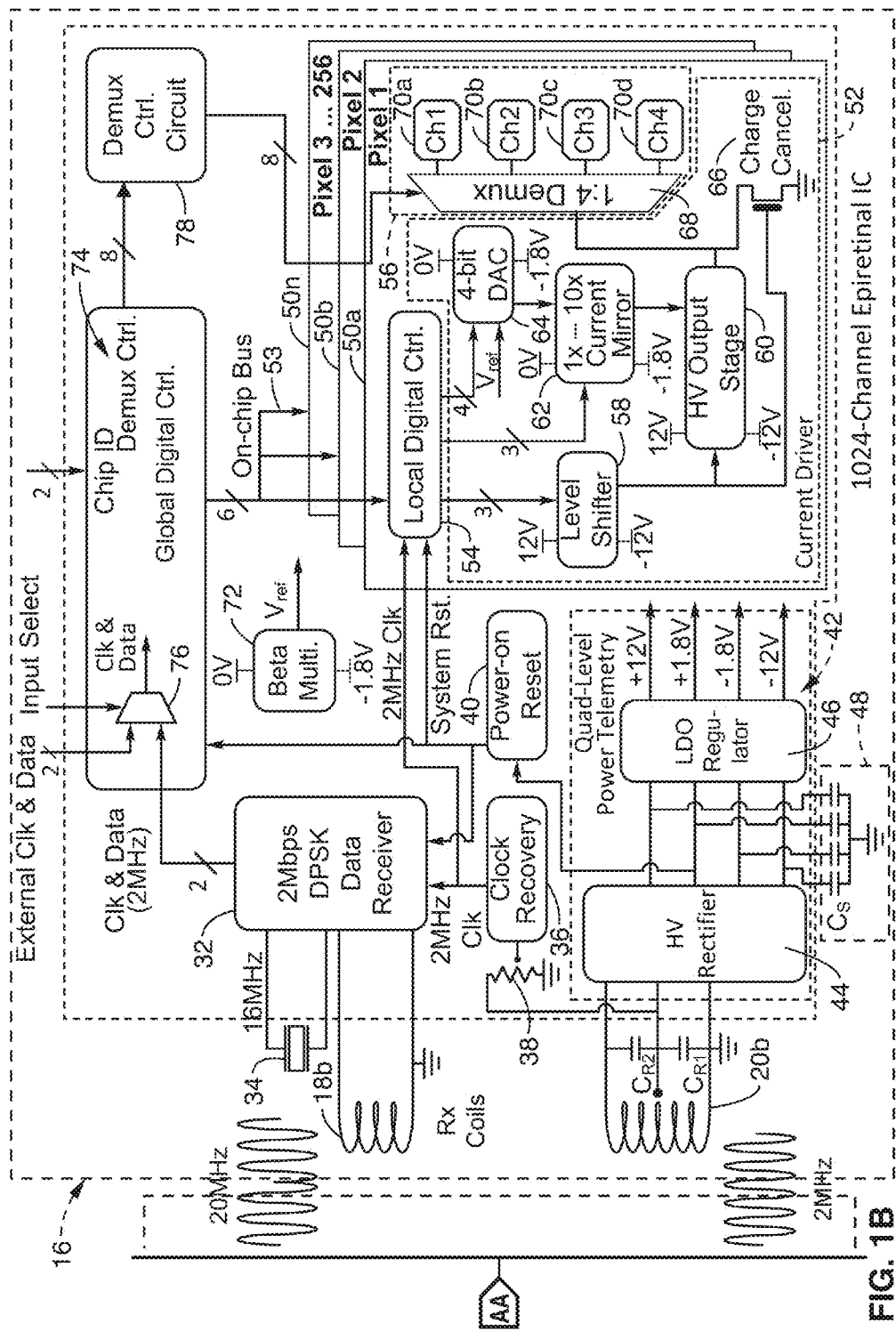

FIG. 1A and FIG. 1B illustrate an embodiment 10 of a high channel count HV stimulator of the invention within an epiretinal prosthesis integrated circuit application.

The epiretinal prosthesis embodiment 10 is shown with camera 12 link 22 to an external circuit 14 (external to the patient's body) for performing data processing 24, data packing 26, and class E drivers 28, 30 for communicating over coils 18a, 18b, 20a, 20b, with a 1024 channel epiretinal IC 16.

The external and implanted circuits are wirelessly coupled, such as preferably inductively linked, for example as depicted here utilizing two pairs of coils. Wireless couplings are necessary to eliminate the need for wiring to the epiretinal device.

In the external circuit, external conditions are registered for communication to the implant circuit. In the present embodiment of a retinal implant, images (sequential images or video) are captured by camera 12 upon which data processing 24 and data packing 26 are performed to convert this information into stimulation parameters based on the individual sensitivity threshold of the patient. This information is then communicated to the prosthetic device, using one or more inductive couplings. The present invention is shown implementing an inductive communication link with two class-E drivers for separately transmitting the data and the power signal to the receiving coils. The power link in this example generates ±12V and ±1.8V (DC) for the chip, and is shown with a class E driver 30 operating through transmit coil 20a for receipt by receive coil 20b, shown with capacitors $C_{R1}$ and $C_{R2}$ coupled to power telemetry circuit 42 in prosthesis 16. By way of example, and not limitation, the inductive power coupling is shown nominally operating at 2 MHz.

Power telemetry circuit 42 preferably comprises a high-voltage rectifier 44 coupled to a low dropout regulator (LDO) 46, with a plurality of storage capacitors 48 between the rectifier and regulator stages. By way of example and not limitation, this power telemetry circuit is multiple voltage levels, which in the described embodiment comprises quad levels, as it generates voltages of ±12 V and ±1.8V, with the low voltage primarily for operating digital circuitry and the high-voltages utilized in the stimulator drive circuits. Another circuit 72 is shown for generating a reference voltage ($V_{ref}$), exemplified as being from the −1.8V supply voltage.

Accordingly, the level shifting circuitry of the inventive implant circuit provides three stage level shifting in which (1) a non-differential first voltage (e.g., +1.8V) is first converted to a differential first voltage (e.g., ±1.8V); (2) which is then converted to a partially differential second voltage (e.g., −1.8V to +12V, or −12V to +1.8V), then to a fully differential second voltage (e.g., ±12V). This second voltage is considered a high-voltage which exceeds the first voltage, and sufficiently high to provide efficient neural stimulation.

Data is transmitted from a class E driver 28 in the external circuit 14 through a transmit coil 18a to a receiver coil 18b, to a data receiver and demodulator 32. By way of example, and not limitation, the data coupling is shown nominally operating at 20 MHz. The present invention is exemplified in the figure utilizing a differential phase shift keying (DPSK) modulation technique, although it should be appreciated that different forms of modulation can be selected (e.g., ASK (OOK), PSK, 8-PSK, 16-PSK, FSK, BPSK, QAM, 16 QAM, 64 QAM, QPSK, DQPSK, 8-DPSK, RZ-DPSK and so forth) without departing from the teachings of the present invention. The receiver and demodulator 32 is seen with a reference oscillator, exemplified utilizing a 16 MHz external crystal 34. Receiver 32 is configured for receiving a recovered clock (e.g., 2 MHz) from the power telemetry circuit 42, through a potentiometer 38 from a voltage tap on coil 20b, to a clock recovery circuit 36. Potentiometer 38 ensures that the amplitude of the 2 MHz power input does not exceed the input voltage range of the clock recovery circuit. By way of example, and not limitation, the implementation shown used a potentiometer ratio of 3/10. The receiver 32 is also configured for receiving a power-on reset circuit 40. Output from the data receiver 32 is coupled to a global digital control (GDC) circuit 74, shown received through a multiplexor 76, which also receives external clock and data, and whose output is selected in response to receiving an input select signal. The GDC programs each neural stimulation output pixel for biphasic stimuli generation and also controls the switching of the 1:4 demux in all pixels. GDC also receives a chip ID signal (e.g., 2 bits), as well as the power-on reset signal. The GDC outputs a demultiplexor control signal (e.g., 8 bits) to a demultiplexor control circuit 78, the output from which is received for controlling demultiplexing within the pixel channels 56. Data from the GDC is sent over an on-chip bus 53 (e.g., exemplified as 6 bits wide) to local digital controller 54, within each pixel 50a through 50n of the 1024 channel epiretinal IC.

It will be appreciated that in view of the retinal prosthesis application being described, the stimulator outputs are recited as being "pixels" although the outputs are actually neural stimulation voltages and not actual image pixels. In other neural stimulation applications these outputs can still be referred to as 'pixels' because the neurons being stimulated are spatially displaced (e.g., typically in a closely-spaced nerve bundle), in some sort of pattern or array which receives neural stimulation based on externally sensed conditions. It should also be appreciated that the conditions sensed by the external circuit may also include or comprise conditions sensed from remote locations on the patient, thus being facilitated by being communicated to the external circuit first and then to the implant circuit.

It should also be appreciated that utilizing the multiplexing circuits of the present invention, allows for multiple neural stimulator outputs to be generated from each so-called 'pixel', thus reducing the necessary circuit area. In the present example embodiment, each of 256 pixels are configured to generate 4 neural stimulation outputs, whereby the retinal SoC provides 1024 stimulation outputs, which are also referred to as channels.

Section 52 represents one out of the 256 channels of stimulation driver. Block 54 comprises a local digital controller (i.e., microcontroller and memory, or logic circuitry, or a combination of logic circuits and programmable elements) which receives the stimulation command from global controller 74 which includes stimulation parameters and control signal for the charge cancellation switch 66. The stimulation parameters are fed to digital to analog converter (DAC) 64 (e.g., 4 bit DAC) in order to determine the minimum stimulus current and to current mirror 62 to provide a scalable current gain from 1× to 10× for output current of DAC 64. Stimulation on/off command signal and the control signal to 66 are amplified through level shifter 58 to ±12V since they are implemented using HV transistors to control HV output stage 60. HV output stage 60 is the current driver which delivers charge to patient tissue through driver block 56. Driver block 56 includes a 1:4 Demux 68 which expands the output channel number from one to four 70a-70d and is implemented using an HV transmission gate. Ultimately, the current stimulus is sent to the tissue under stimulation through electrodes 70a-70d.

Figure 2:
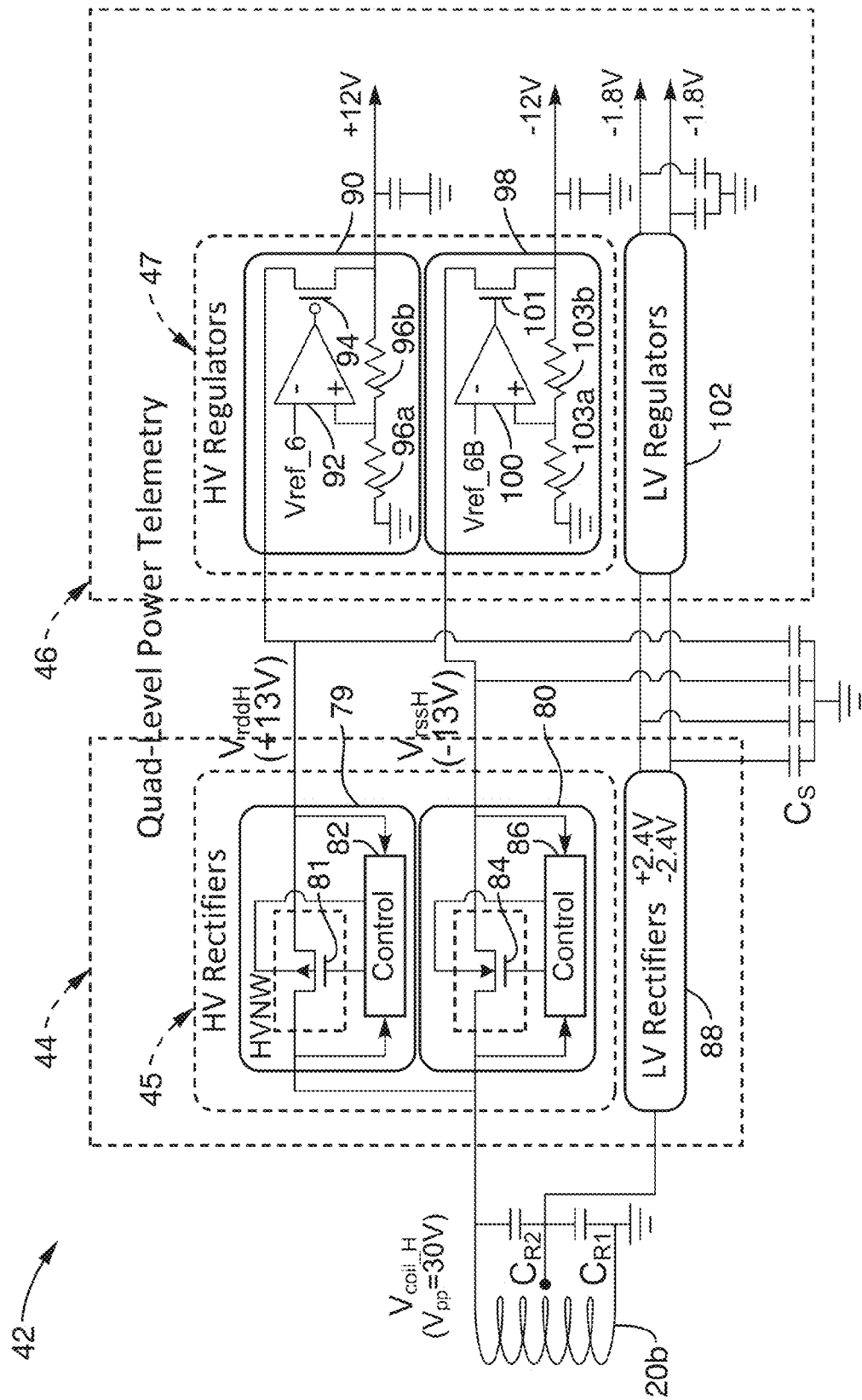
FIG. 2 is a schematic of quad-level power telemetry for use in the high-voltage stimulator circuit according to an embodiment of the present invention.

FIG. 2 illustrates an example embodiment 42 of a quad-level power telemetry link, having a rectifier section 44 and regulator section 46, designed to reduce overall power consumption by using mixed-voltage operation. Quad-level power circuit 42 is shown comprising HV rectifier section 45 and an HV regulator section 47 between which are disposed a plurality of capacitors ($C_S$). The circuit avoids the use of off-chip diodes for power rectification, and utilizes a transistor-based timing-controlled rectifier to improve integration and voltage conversion efficiency (VCE). The present invention overcomes design issues of the HV rectifier, including substrate leakage, long HV switch transition time, reverse leakage current and circuit startup.

The HV rectifier 45 is shown with a first source 79 ($V_{rddH}$) and a second source 80 ($V_{rssH}$) implemented with TSMC triple-well CMOS shown with a PMOS transistor 81 and NMOS transistor 84. A leakage current is formed through the parasitic bi-polar junction transistor (BJT) from the PMOS drain in the HV n-well (HVNW), to the P− substrate, when the input voltage $V_{coil\_H}$ exceeds HVNW by a diode turn-on voltage. The BJT is always kept off by a dynamic substrate-biasing scheme, which pulls the HVNW voltage to either $V_{coil\_H}$ or $V_{rddH}$, whichever is higher. The VCE is improved by turning on the rectifying switch with a boosted gate control voltage ($V_{rssH}$ at −13V). The source voltage of the PMOS is $V_{coil\_H} \geq 13V$ and the $|V_{GS}| > 26V$, so the $V_{DS}$ drop across the rectifier is reduced, leading to a high VCE. The gate control signal has a long transition time ($t_{Lag}$) due to the large gate capacitance of the HV transistors and the large signal swing. In order to turn on the switch precisely when $V_{coil\_H} > V_{rddH}$, the gate controllers 82, 86 toggle at $V_{th}$ with $t_{Lag}$ ahead of $V_{coil\_H} = V_{rddH}$. The gate controllers 82, 86 also ensure the PMOS switch is off before $V_{coil\_H} < V_{rddH}$, thus eliminating the reverse leakage current. At startup, a diode-connected PMOS 81 charges up $V_{rddH}$ until the gate controller activates the PMOS switch. By way of example and not limitation, a similar rectifying mechanism is implemented in low-voltage rectifier 88.

Output from the HV and LV rectifiers is received by a regulator section 46, having a high-voltage regulator section 47 and a low voltage regulator section 102. HV regulator 47 is shown having a positive regulator 90 and a negative regulator 98. The positive regulator is seen with a regulator circuit 92 receiving a reference voltage (e.g., $V_{ref\_6}$) driving output transistor 94 in response to feedback from a feedback circuit, shown exemplified with resistors 96a, 96b to output +12V to which is coupled bypass capacitor $C_{OUT}$. Similarly, the negative regulator is seen with a regulator circuit 100 receiving a reference voltage (e.g., $V_{ref\_6B}$) driving output transistor 101 in response to feedback from a feedback circuit, shown exemplified with resistors 103a, 103b to output −12V to which is coupled another bypass capacitor $C_{OUT}$. The schematic for the LV regulator 102 can be similarly configured for outputting a positive and negative low voltage (e.g., ±1.8 volts) and having similar bypass capacitors $C_{OUT}$.

FIG. 3A illustrates an example embodiment 82 of a rectifying switch control circuit, as was seen in 82, 86 of FIG. 2. FIG. 3B depicts an example 126 of a delay circuit depicted in FIG. 3A. Referring to FIG. 3A, inputs 106 are shown for $V_{coil\_H}$ and $V_{rddH}$ received at a startup circuit 108, exemplified as a diode-connected transistor designed to provide initial voltage for operation of level shifter 130. Beyond the startup circuit, voltages $V_{coil\_H}$ and $V_{rddH}$ are received at circuit 110 which performs dynamic substrate biasing in response to cross coupled transistors 112a, 112b to output substrate voltage HVNW 114. Voltages $V_{coil\_H}$ and $V_{rddH}$ are also received through respective resistive ladders comprising resistors 116a, 116b and 118a,118b, to a look ahead gate controller 120. Gate controller 120 comprises a comparator 122 comparing a $V_{Th}$ portion of $V_{rddH}$ to a portion of $V_{coil\_H}$. Comparator output (signal a) is received along a first path by an inverter 124, and by a second parallel path by a delay 126, with outputs (signal b) and (signal c) received by a NOR gate 128 which outputs a logical signal (signal d). The logical signal (signal d) is boosted in voltage by a level shifter 130, to new drain and source supply rails $V_{rddH}$ and $V_{rssH}$ to generate boosted gate control signals 132 (signal e).

FIG. 3B illustrates one simple embodiment of a digital delay circuit 126, shown by way of example and not limitation, as it will be appreciated by one of ordinary skill in the art that there are numerous ways to generate digital time delays (e.g., timer circuits, delay lines, synchronous circuits, and so forth). The example delay is shown comprising multiple stages 134a through 134n, in at least one embodiment of the invention this comprises six stages. Each stage is shown comprising an inverter 136a . . . 136n coupled to a capacitor 138a . . . 138n at the output.

Figure 4:
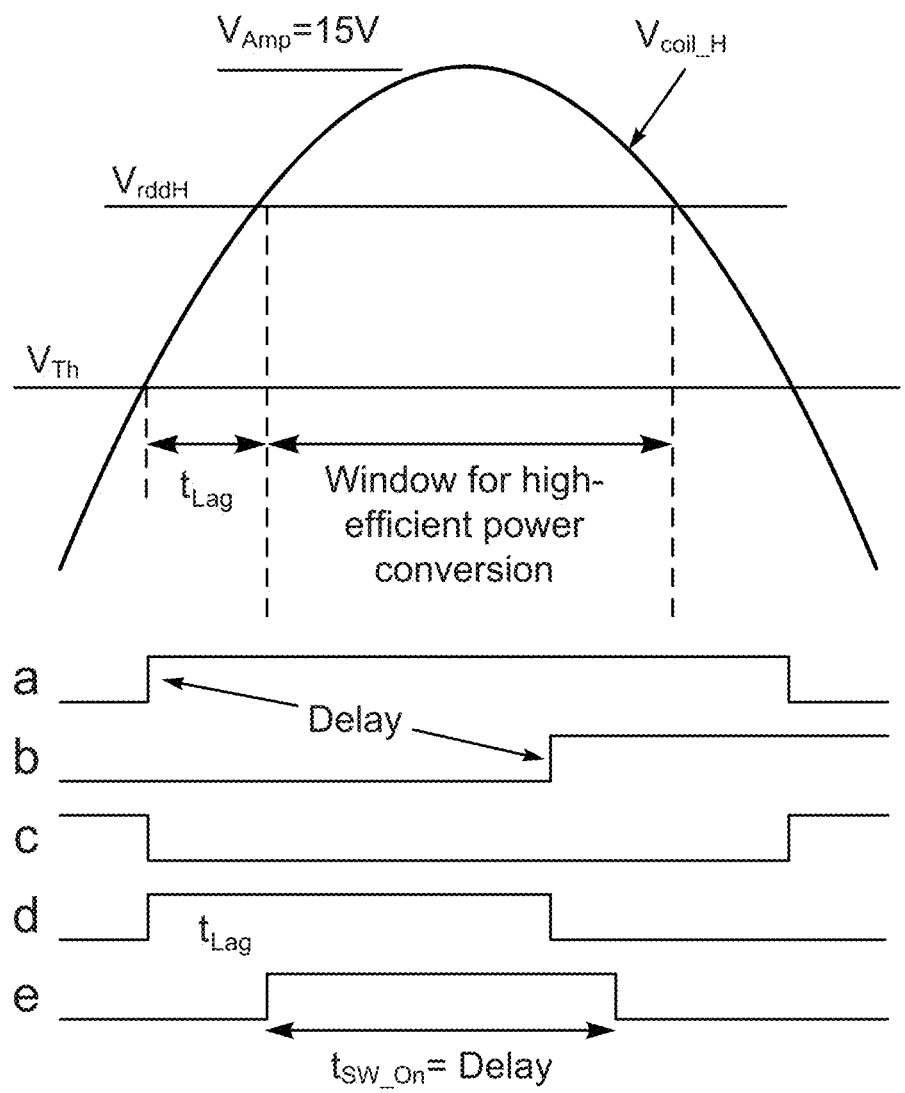
FIG. 4 is a plot and timing diagram showing power conversion aspects according to an embodiment of the present invention.

FIG. 4 depicts timing waveforms which take place within a timing window that provides high efficiency power conversion. At the top portion of the figure a portion of the coil voltage waveform is shown, with voltage $V_{Th}$ reached first, and after a time delay $t_{Lag}$ the coil reaches voltage $V_{rddH}$ and the high efficiency power conversion window is reached, after which coil voltage reaches its 15V maximum, and then slopes off through $V_{rddH}$ and $V_{Th}$.

Timing signals at the bottom of FIG. 4 denote the signals (a)-(e) shown in the look-ahead gate controller 120 seen in FIG. 3B. Comparator 122 in FIG. 3B is activated when $V_{coil}$ exceeds $V_{Th}$, whereby at that time both signals (b) (c) are logic low causing gate 128 to be active (logic high) for a period of time equal to the delay, whereby as (b) drops low after the delay then (d) also drops to low. Output (d) is shown in the boosted gate control signal (e) after $t_{Lag}$ of the level shifter.

Figure 5A:
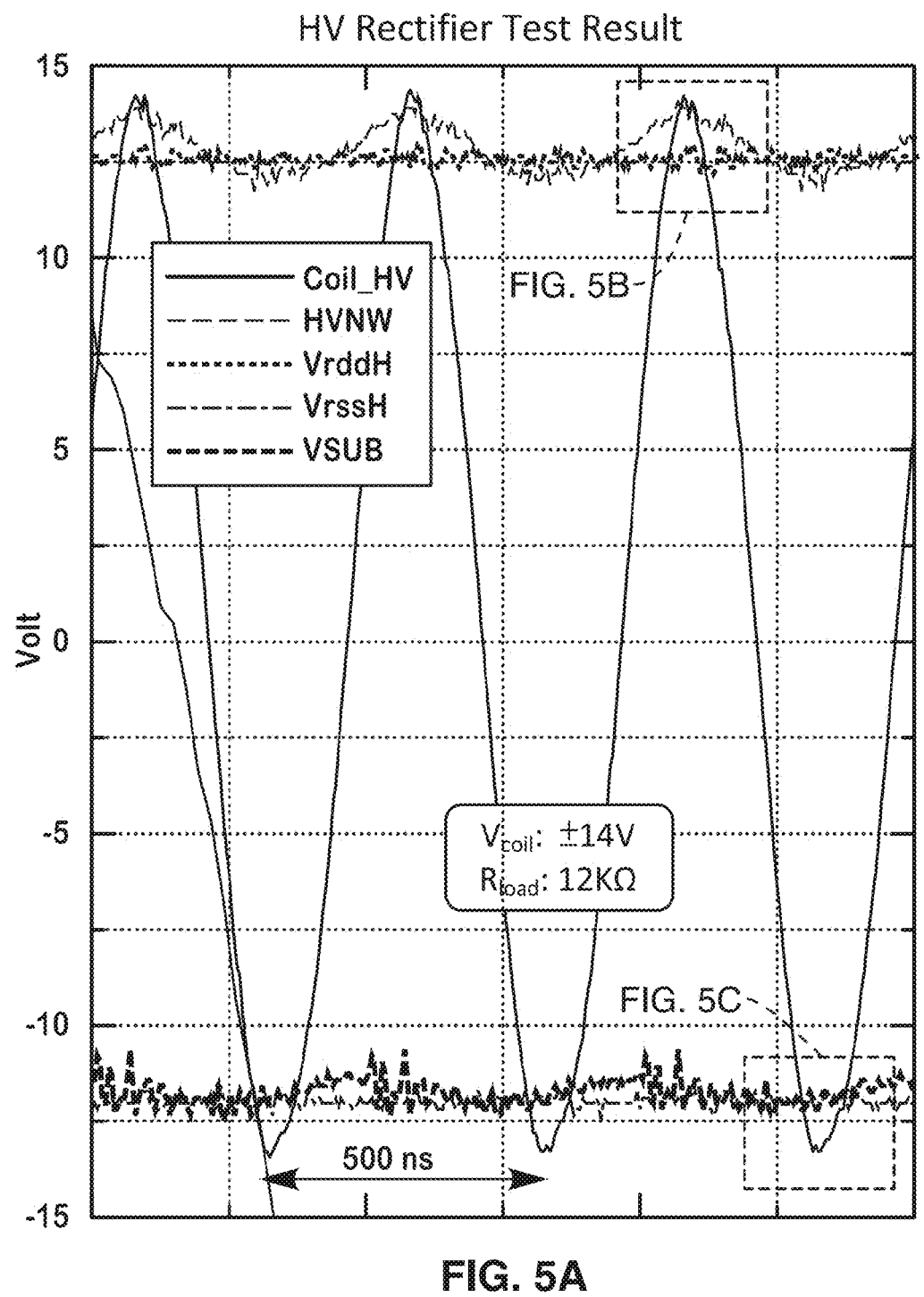
FIG. 5A through FIG. 5C are plots of high-voltage test results according to an embodiment of the present invention, showing various voltages in FIG. 5A, with specific portions magnified in FIG. 5B and FIG. 5C.
Figure 5B:
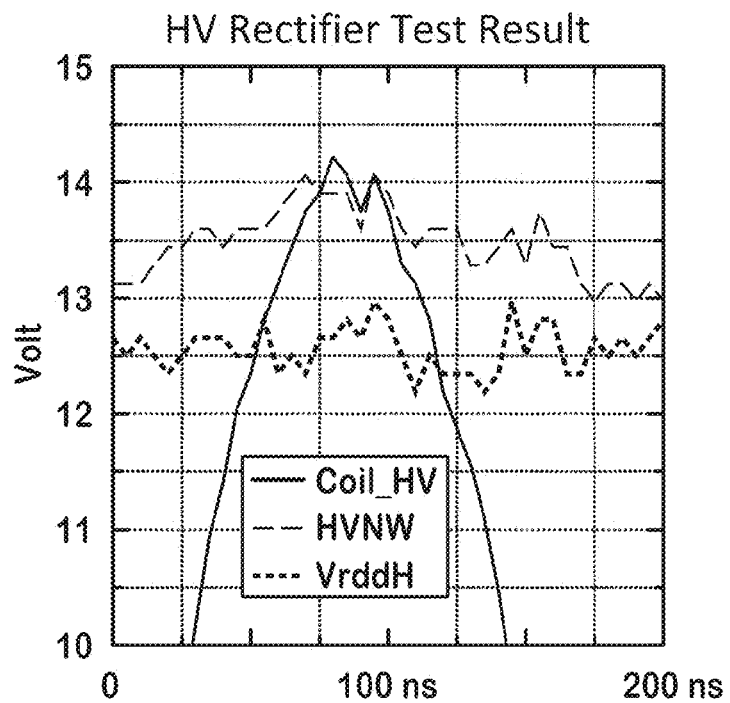
Figure 5C:
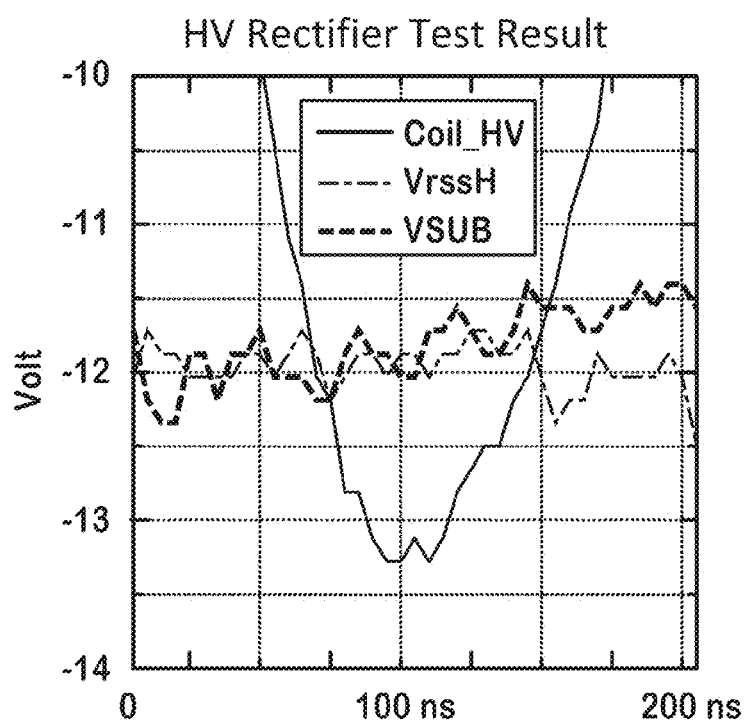

FIG. 5A through FIG. 5C is a measured waveform verifying performance of the high-voltage rectifier, and showing signals Coil_HV, HVNW, $V_{rddH}$, $V_{rssH}$, and $V_{SUB}$. Voltage HVNW 114 is the substrate voltage for the transistors of HV rectifier, while voltage $V_{SUB}$ is the substrate voltage of the entire chip. Different load conditions of the HV rectifier are characterized by varying the loading resistor, while the induced coil voltage is fixed at ±14V. Specifically, the output power of 50 mW corresponds to a 12 kΩ load and the |$V_{rddH}$−$V_{rssH}$| is 24.5V (87.5% VCE). A peak and valley of FIG. 5A are seen magnified in FIG. 5B and FIG. 5C respectively, reaching about +14V, and −13.5V respectively.

Figure 6:
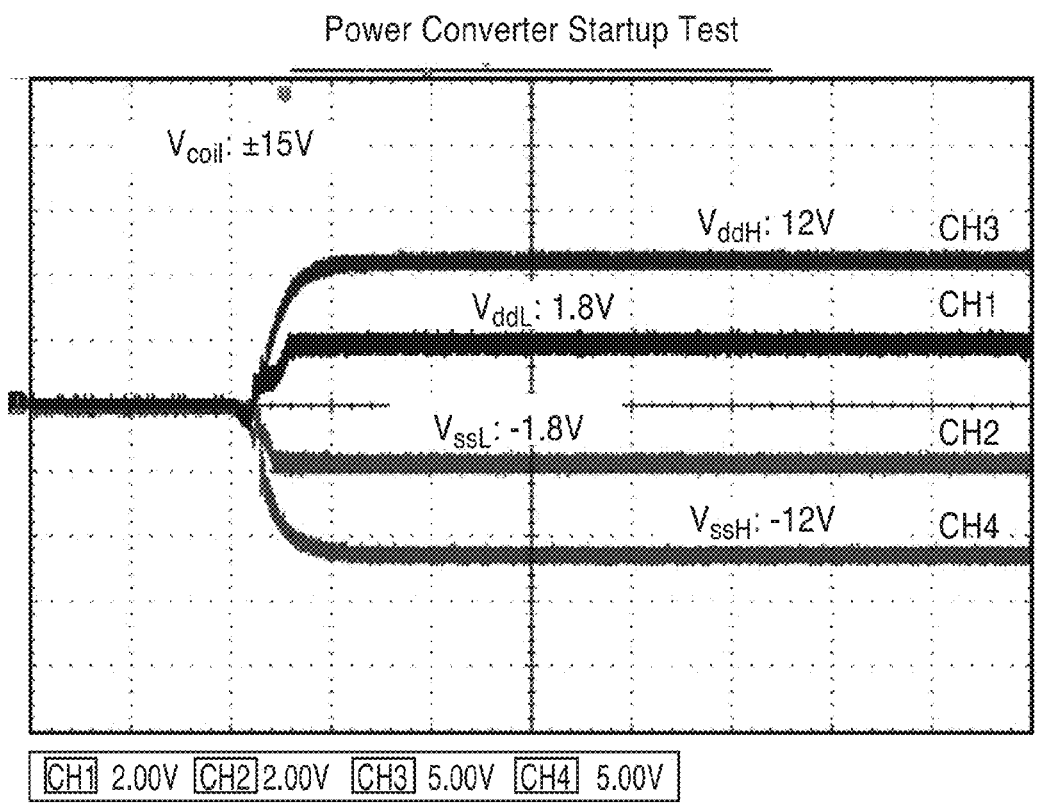
FIG. 6 shows waveforms found for a power converter startup test according to an embodiment of the present invention.

FIG. 6 illustrates power converter startup, with a scale of 100 µs per division, wherein it is seen that output voltages ($V_{ddH}$, $V_{ssH}$, $V_{ddL}$, $V_{ssL}$) of the power link are stabilized within less than 100 µs of startup.

Figure 7:
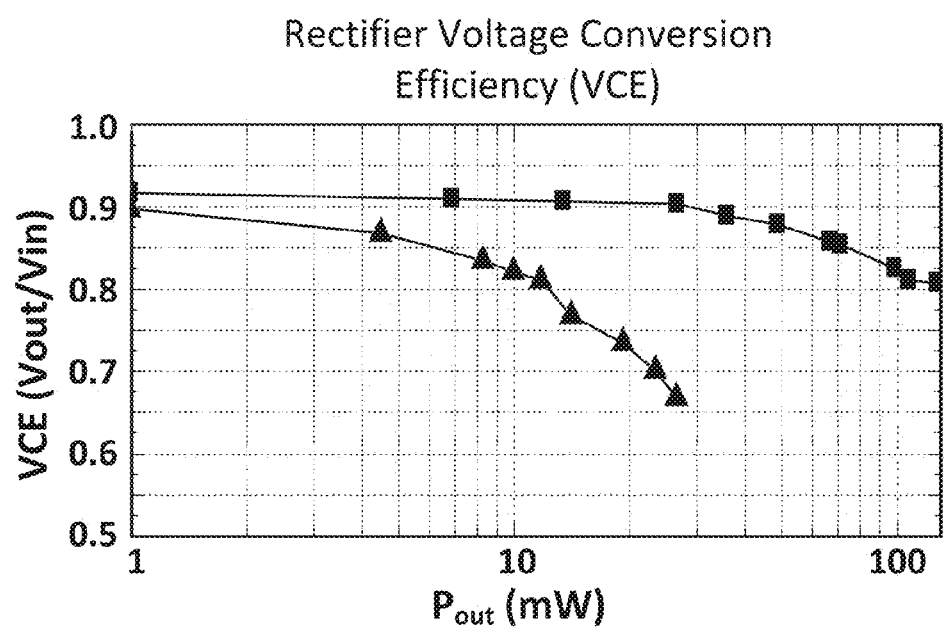
FIG. 7 is a plot of rectifier voltage conversion efficiency comparing HV and LV rectifiers utilized according to an embodiment of the present invention.

FIG. 7 illustrates rectifier voltage conversion efficiency (VCE), for both the LV and HV rectifier. It will be noted that VCE is still 83% at an output load of 98.8 mW for the HV rectifier. The LV rectifier utilizes far less power than required by the HV rectifier, and less benefit is derived from very high power conversion efficiency in the LV rectifier. The power converter design of the present invention is able to support at least four voltage levels.

It will be appreciated that DPSK provides substantial levels of interference-rejection and is well suited for use in the inventive retinal prosthesis. In this SoC, the capacitor arrays are optimized, and the bit-error ratio (BER) is further improved by: (a) a 2nd-order high-pass filter (HPF) to suppress power signal interference, (b) a programmable threshold voltage, and (c) a non-ideal sample-exclusion scheme (NSE). NSE reduces the integration noise resulting from the phase transition. The programmable threshold voltage is used as a threshold to distinguish the incoming data (e.g., bit 1 or bit 0), and it can be adjusted based on the quality of the data link. If the noise is high (poor link quality), then the threshold voltage can be set higher to suppress noise influence.

Figure 8A:
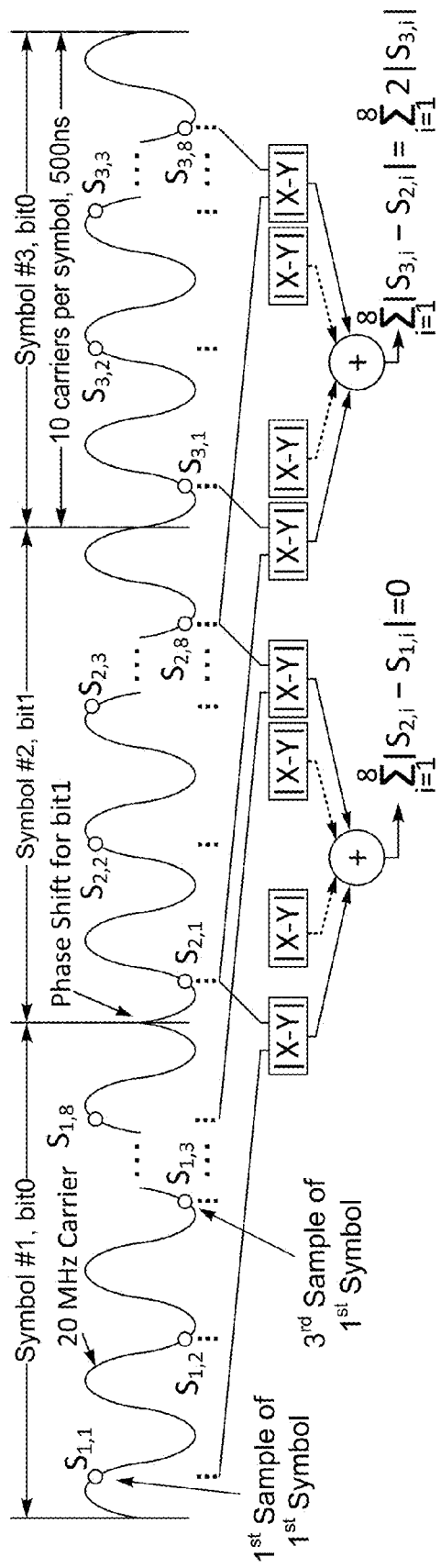
FIG. 8A through FIG. 8C are diagrams, plots and waveforms of phase transitions in a DPSK signal found according to an embodiment of the present invention.
Figure 8B:
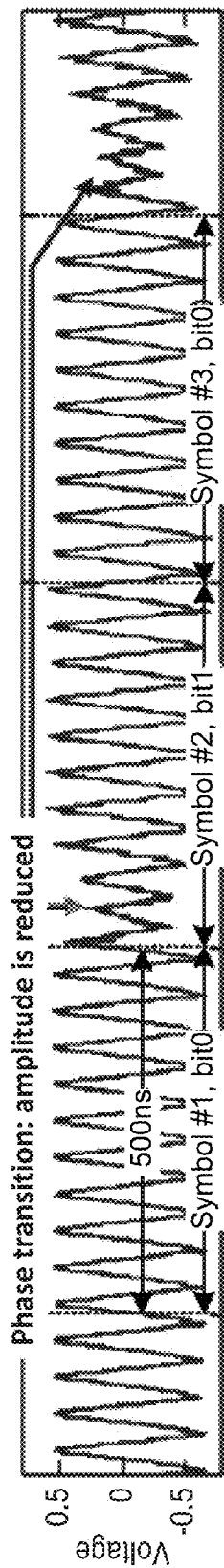
Figure 8C:
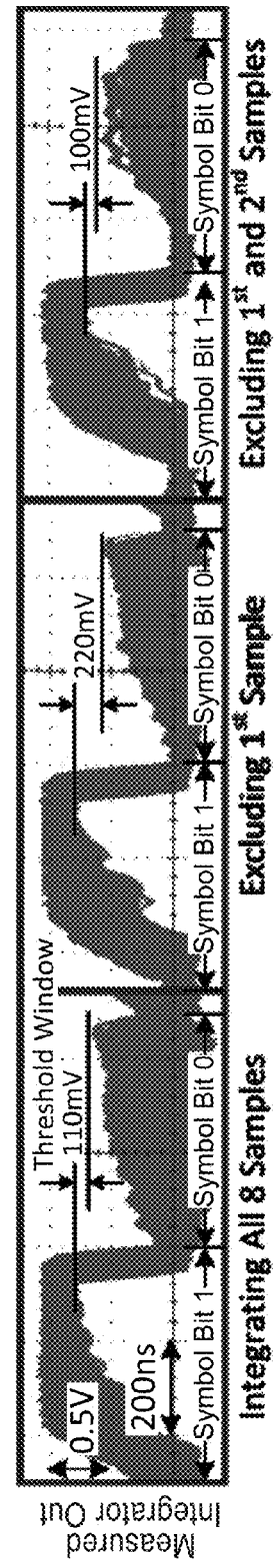

FIG. 8A through FIG. 8C depict signaling performed using a carrier modulation communication technique, exemplified as differential phase shift keying (DPSK), which is utilized within at least one embodiment of the present invention. Phase shift keying is seen in an ideal DPSK signal in FIG. 8A having a phase change to represent bit 1 and no phase change for bit 0, where $S_{i,j}$ means $j^{th}$ sample of $i^{th}$ symbol. Eight samples are acquired per DPSK symbol using 16 MHz clock and 2 Mb/s data rate. By sampling two consecutive symbols, the DPSK receiver calculates the absolute symbol and its previous one. The difference is then integrated to determine whether this incoming symbol is bit 1 or bit 0. The embodiment shown utilizes a subsampling (bandpass sampling) technique such that the sampling rate can be smaller than the carrier frequency. Thus, a high frequency clock source (e.g., crystal oscillator) which consumes more power than a low frequency one is not required.

In FIG. 8B a real DPSK signal is depicted in which the phase transition between symbols of different logic levels is indicated with arrows where amplitude is reduced. As seen in FIG. 8B the phase transition of this real DPSK signal takes about 100 ns, whereby samples obtained near the transition compromise integration output, thus resulting in a smaller threshold voltage window.

In FIG. 8C, waveforms are depicted as obtained for non-ideal sample exclusion, with all 8 samples integrated at left of the figure, excluding the first sample seen at the center of the figure, and excluding both first and second samples as seen at the right portion of the figure. It will be seen that by excluding the first sample, a threshold window of 220 mV is obtained, whereas only 110 mV is provided without exclusion, or with first plus second sample exclusion. Thus, by excluding the first sample from the integration, the threshold window is increased by 100%. The embodied SoC allows users to exclude 0 to 2 samples depending on the condition of the inductive link.

Figure 9:
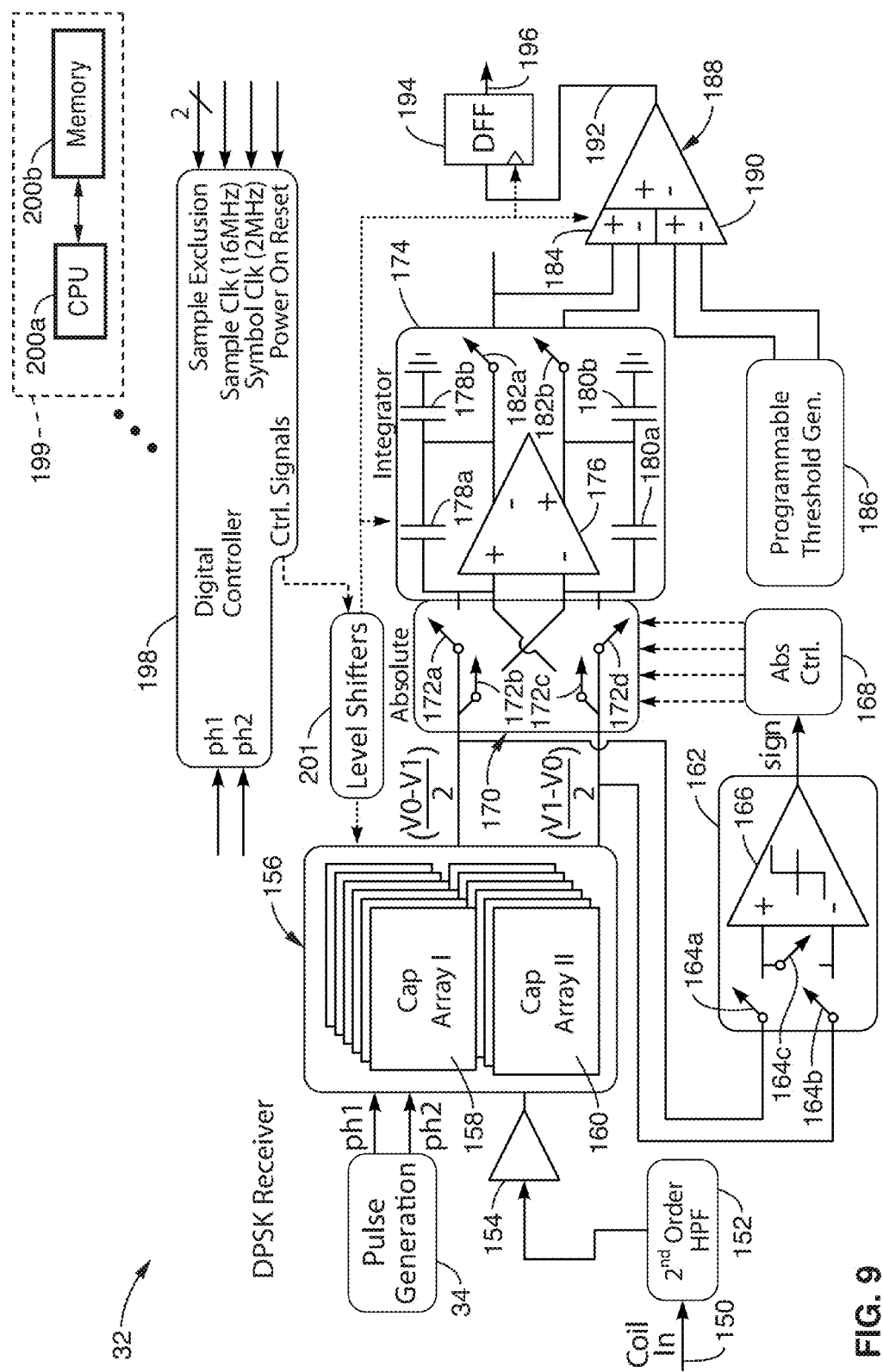
FIG. 9 is a schematic of a DPSK receiver according to an embodiment of the present invention.

FIG. 9 illustrates an example embodiment 32 of a DPSK receiver of the present invention. Pulse generation 34 is seen coupled to the DPSK device, with phase 1 and phase 2 signals, and is configured to generate two non-overlapping clock signals for sampling. In this example embodiment, input to pulse generator 34 is from a 16 MHz crystal as seen in FIG.

1B. One terminal of coil 18b, seen in FIG. 1, is connected to a coil in line 150 to a high pass filter (HPF) 152, in this case exemplified as a second order HPF. Output from the HPF is then preferably buffered 154 before receipt by the capacitor arrays 156, preferably comprising group 1 array 158 and group 2 array 160, as described in the previous section. Output from the arrays comprise signal (V0−V1/2) and (V1−V0/2) which is received by a sampling circuit 162 which outputs a sign value to an absolute value control circuit 168. Switches 164a, 164b, 164c at the input of a comparator 166 provide control of sampling and resetting the comparator input in sampling circuit 162.

Signals (V0−V1/2) and (V1−V0/2) and digital control output from circuit 168 are received by an absolute value switching circuit 170 comprising series switches 172a, 172d, and cross-connect switches 172b, 172c, thus allowing the voltage between (V0−V1/2) and (V1−V0/2) to be switched into a positive polarity before receipt by a differential integrator circuit 174.

Integrator 174 is shown comprising a differential operational-amplifier (op-amp) 176 with capacitive feedback capacitors 178a, 178b, 180a, 180b. Switches 182a, 182b are in series on the outputs of the differential output to control whether the integrated signal is passed along or not. Differential output from integrator 174 is received at a first pair 184 of inputs to a programmable comparator 188, which also receives at a second pair of inputs 190, a programmable threshold as a differential signal from programmable threshold generator 186.

A digital output 192 from comparator 188 is received at a data latch 194 (e.g., D flip-flop), within which the logic state is latched to generate output 196, in response to receipt of a clock signal from a digital controller 198.

Digital controller 198 is shown for receiving the generated pulses (ph1, ph2), as well as sample exclusion bits, a sample clock, a symbol clock and a power-on reset signal, based on whether it controls various operations in the system. Control outputs include a clock to data latch 194, control of integrator switches 182a, 182b, a reset signal to the differential comparator 188 and outputting control signals to level shifters 201 whose outputs are coupled to the capacitor arrays 156. At least one embodiment of digital controller 198 incorporates processor circuitry 199, such as including a microcontroller 200a (e.g., CPU, microcontroller (uC), microprocessor (uP), digital signal processor (DSP), field-programmable gate array (FPGA), processor enabled application specific device (ASIC), or other programmable digital circuit), and memory 200b.

Figure 10A:
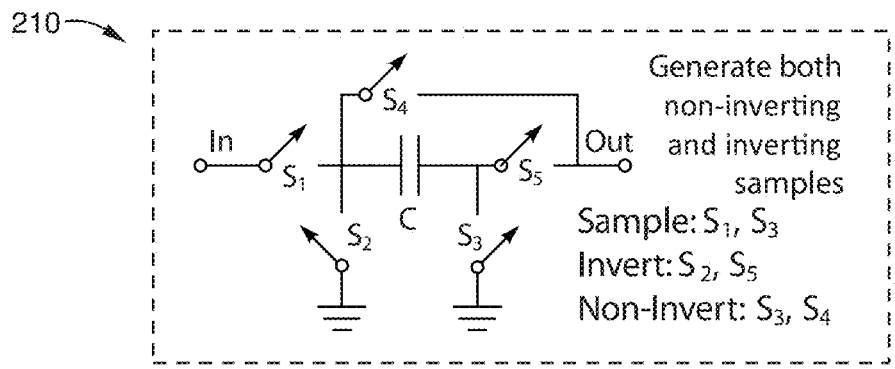
FIG. 10A through FIG. 10C are block diagrams comparing area efficient switched capacitor configurations utilized according to at least one embodiment of the present invention.
Figure 10B:
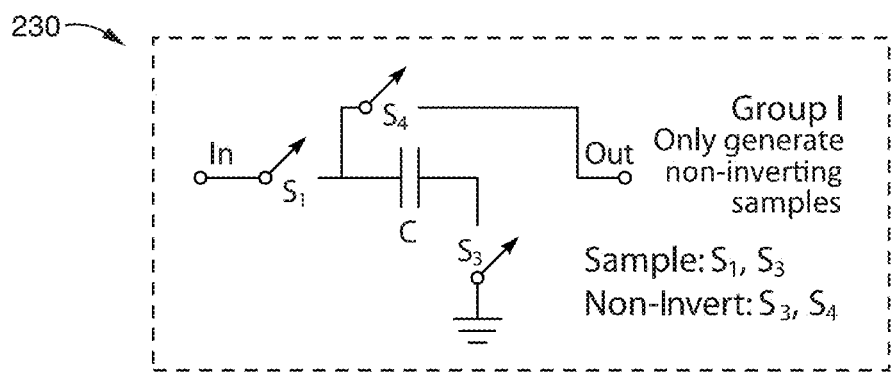
Figure 10C:
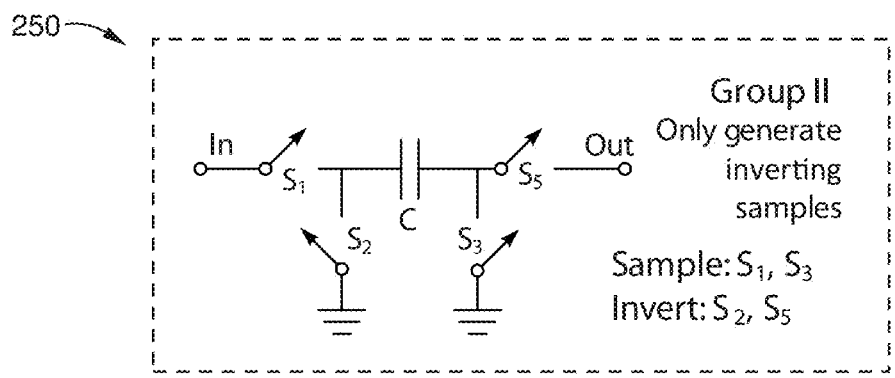

FIG. 10A through FIG. 10C compare switched-capacitor arrays, that may be utilized according to the invention, each showing a single capacitor (C), with switches between an input (In) and output (Out). In conventional receiver switched capacitor arrays FIG. 10A, each capacitor array unit traditionally has to support both inverting and non-inverting operations. The switched capacitor design 210 in FIG. 10A illustrates a single capacitor switched through five switches per capacitor unit. It will be noted that 48 units are required in the system. Switches $S_1$ and $S_3$ are for sampling, with $S_2$ and $S_5$ for inverting samples and $S_3$ and $S_4$ for non-inverting samples. Optimizing the capacitor (cap) array operation flow divides the capacitor units into two groups, as seen in FIG. 10B and FIG. 10C, in which each group need only manage one operation. This reduces the overall number of switches and their corresponding level shifters by 30%. FIG. 10B depicts a Group 1 embodiment 230 for generating non-inverting samples, comprising a single capacitor C, switches $S_1$ and $S_3$ for sampling, and $S_3$ and $S_4$ for non-inverting samples. Thus, only three switches are required compared to the five need in FIG. 10A, thus a 40% reduction is achieved. FIG. 10C depicts a Group 2 embodiment 250 for generating inverting samples, comprising a single capacitor C, switches $S_1$ and $S_3$ for sampling, and $S_2$ and $S_5$ for inverting samples. Thus, only four switches are required compared to the five needed in FIG. 10A, thus a 20% reduction is achieved. The overall 30% savings in switches can be substantial, considering that 24 Group 1 switched capacitor units and 24 Group 2 switched capacitor units are required in the system.

Figure 11:
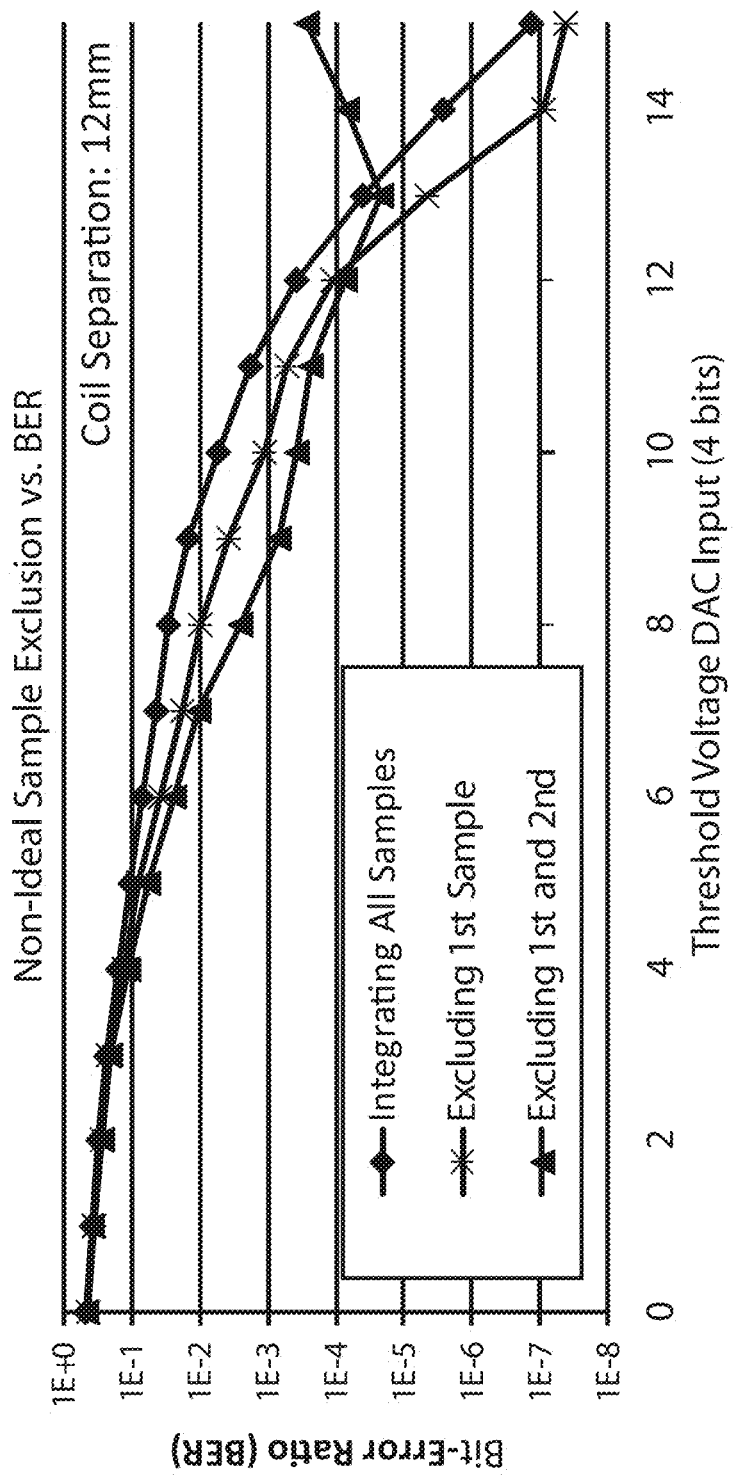
FIG. 11 is a plot of bit error rate (BER) found utilizing an embodiment of the present invention, showing a comparison between integrating all samples, excluding the first sample and excluding the first and second sample.

FIG. 11 depicts test results for the DPSK receiver seen in FIG. 9, which provides a bit error rate (BER) of less than $10^{-7}$ when excluding the first sample from the integration.

Figure 12A:
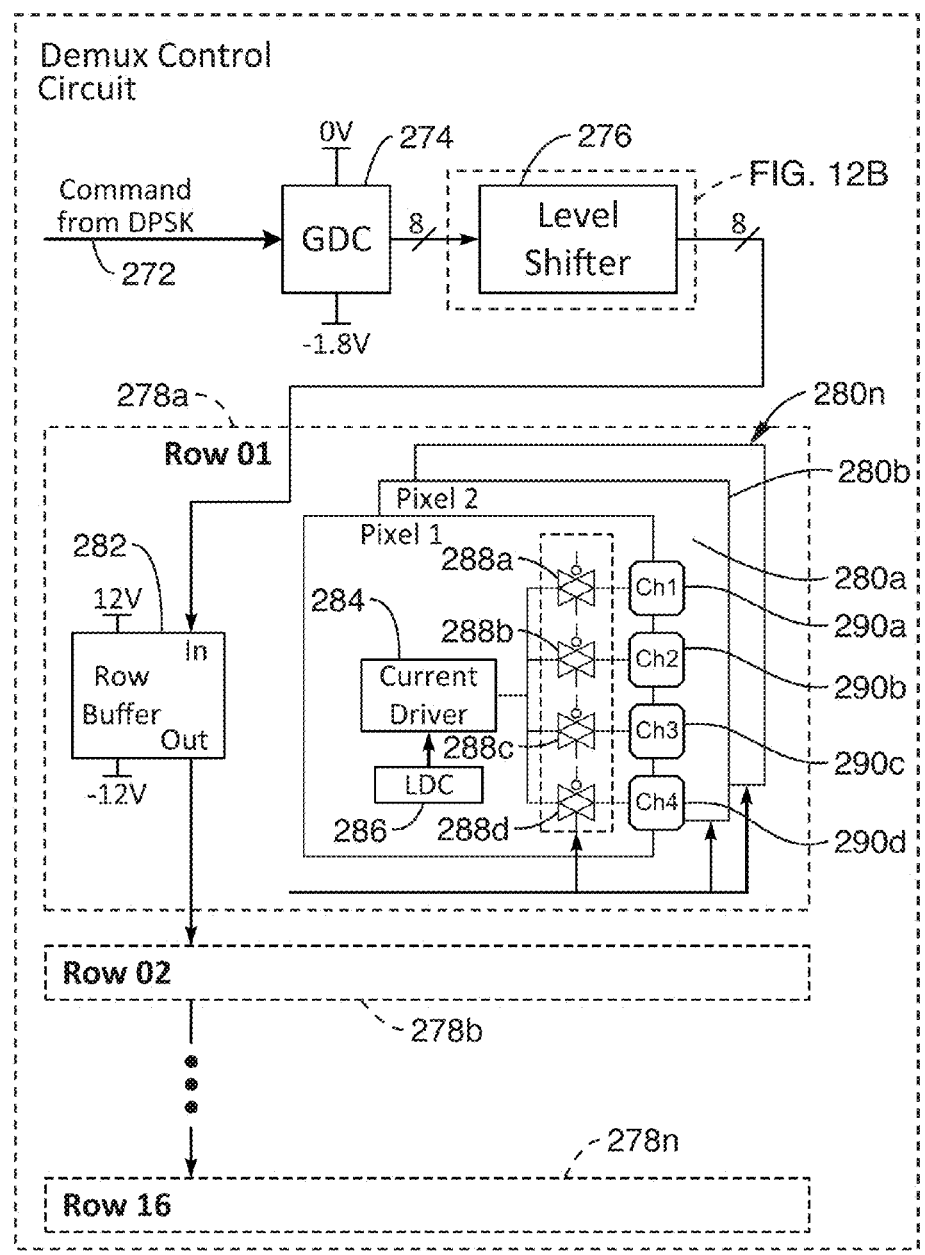
FIG. 12A through FIG. 12C depict a block diagram/schematic/and bar plot for a demultiplexor control circuit utilized according to an embodiment of the present invention.
Figure 12B:
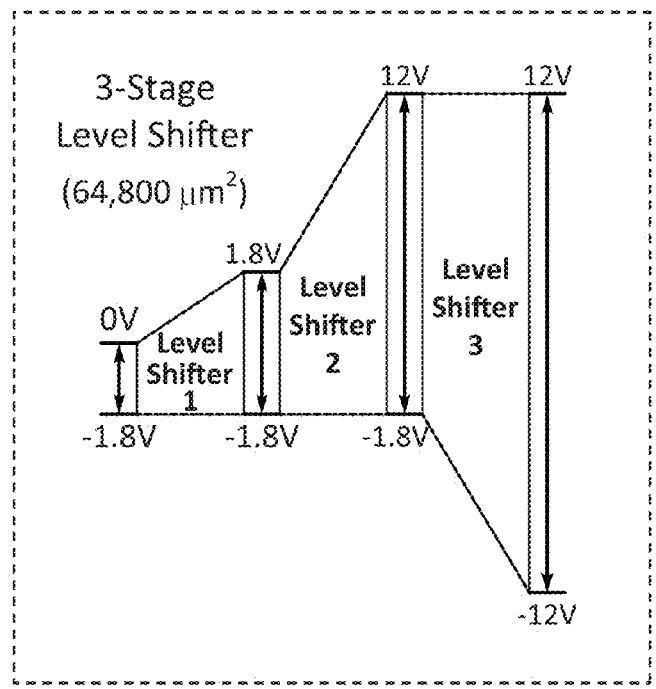
Figure 12C:
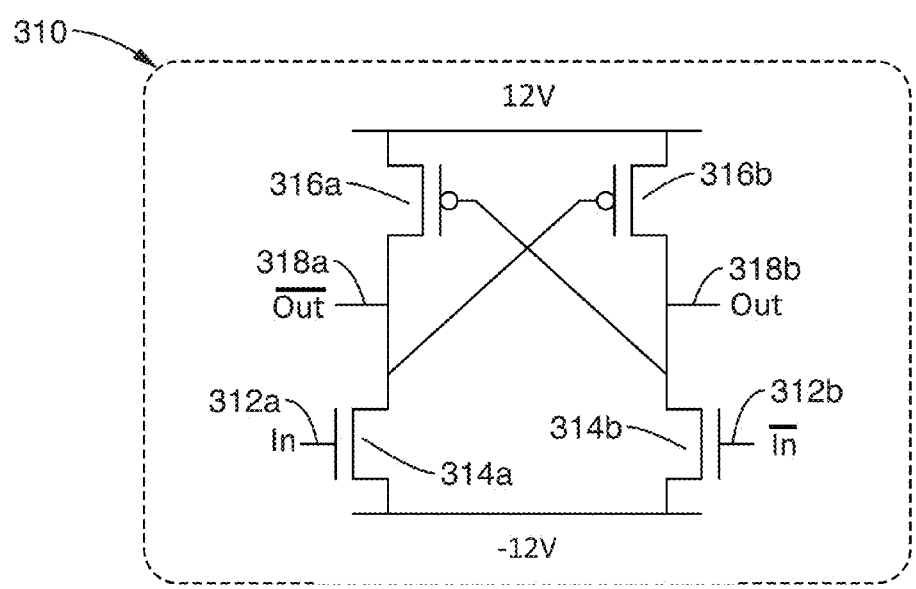

FIG. 12A through FIG. 12C illustrate an example embodiment demultiplexor 270 in FIG. 12A, chart of shifted levels in FIG. 12B, and level shifter 310 in FIG. 12C.

One of the key challenges in scaling up the number of stimulation channels is the chip size limitation. Demultiplexor and chip clustering is seen in FIG. 12A for scaling to overcome these chip size limitations. A 1:4 demux lets each "pixel" of the output to support 4 channels by sharing 1 current driver, instead of having to integrate a separate current driver for each output. The area of a demux is small, but the high compliance voltage requires 4 area-consuming level shifters (LS) to boost the demux control signals from 1.8V to 24V. Thus all demultiplexors (demuxes) on the chip are controlled globally by only one set of LSs. This SoC also supports chip clustering for scaling. Each of the 1024 pixels in the 4-SoC system is accessible using a 10 bit address: 2 bits for the chip ID and 8 bits for the pixel address. Thus, the array can support 4096 individual channels.

Referring to FIG. 12A, a command is received 272 from the DPSK to a global digital control (GDC) circuit 274, which outputs digital control lines (e.g., 8 digital lines) to a level shifter 276. Output from the level shifter 276 is received at a row buffer 282 for a first row (Row 01) 278a, with similar buffers for rows 278b . . . 278n (Rows 2 through 16). There are 16 row buffers in this embodiment. Each row buffer relays the demux control signal to 4 stimulation pixels 280a . . . 280n, which in turn each have 4 channels. Accordingly, 16 channels are provided in each row. The demux control circuitry thus operates in a 16×16 manner, with 16 rows each having 16 channels. Each row 278a-278n relays the demux command signals to 16 stimulation channels. In each channel, demux 288a, 288b, 288c, 288d passes the stimulation current provided from current driver 284, with its parameter set by the local digital controller 286, to the electrode selected 290a, 290b, 290c, 290d. Using this approach, the channel number in one stimulation driver can be expanded four times with minimal area increment.

FIG. 12B depicts 3 stages of the level shifter, from a voltage of +1.8V to ±1.8V in a first shift; then from ±1.8V to +12V/−1.8V in a second shift; then from +12V/−1.8V to ±12V in the third shift. It should also be appreciated that the second shift can be similarly configured to reach +1.8V/−12V, without departing from the teachings of the invention. It should also be appreciated that different voltage levels may be utilized for these low and high voltages without limitation.

Referring to FIG. 12C is a level shifter circuit embodiment 310, configured for performing the third level shift bringing the output to the high-voltage supply rails, which in this example are ±12V. It will be noted that the circuit area for the exemplified level shifter is 64,800 μm. In the level shifter circuit, two parallel transistor stacks are coupled between the high-voltage drain (12V) and source (−12V). The first stack comprises PMOS transistor 316a, in series with NMOS transistor 314a, while a second stack has PMOS transistor 316b, in series with NMOS transistor 314b. The respective gates of the PMOS transistors are cross-coupled to opposing drains of the NMOS transistors, where complementary outputs (Out and $\overline{\text{Out}}$) are shown 318a, 318b. Complementary inputs (In and $\overline{\text{In}}$) 312a, 312b are coupled to the respective gates of NMOS transistors 314a, 314b.

Figure 13:
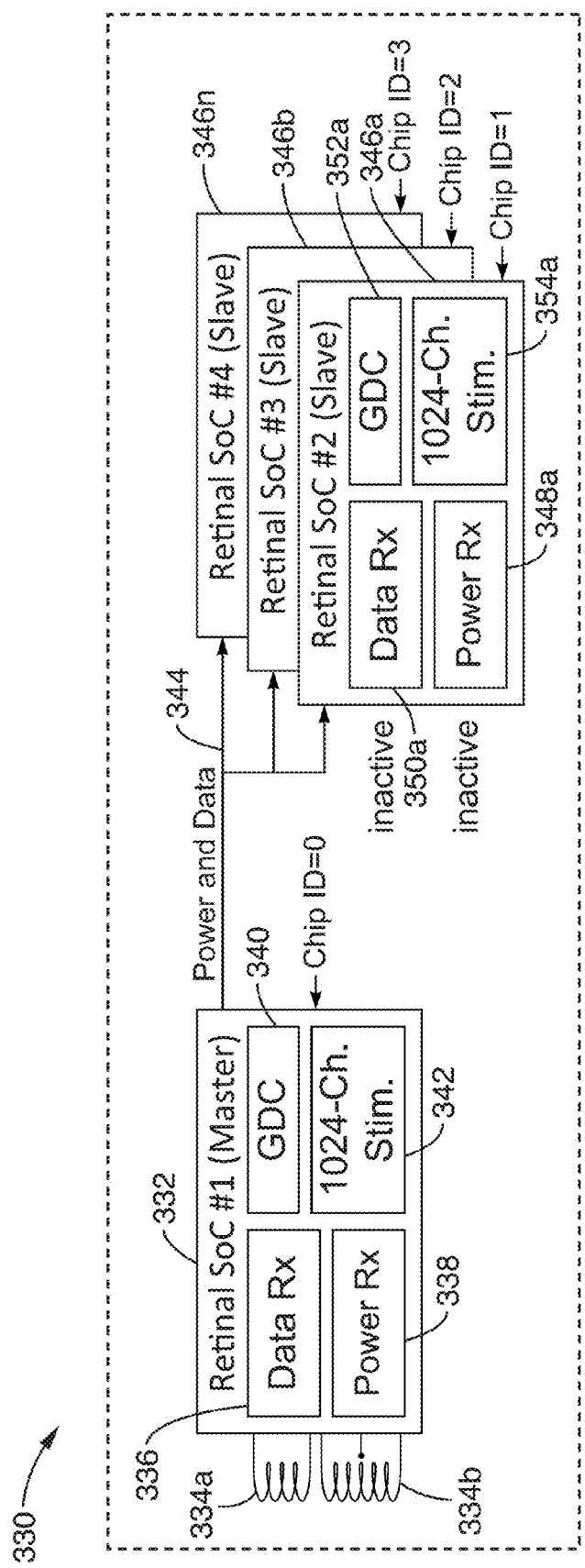
FIG. 13 is a block diagram of chip clustering according to an embodiment of the present invention.

FIG. 13 illustrates an example embodiment 330 of inventive chip clustering, which allows scaling up the stimulator prosthesis, such as up to 4096 electrodes in this example embodiment. It will be appreciated that the clustering mechanism can be utilized for scaling up the stimulator to other levels, such as 2×, 3×, and more than 4×, depending on the application, with the approach itself being scalable toward achieving any desired level of clustering. In the example shown, four retinal SoCs 332, 346a, 346b, 346n are seen interconnected in the figure.

One of the SoCs, in this case SoC 332, operates as the master device configured to connect to coils 334a, 334b, for communicating (receiving) power and data with the external circuit, and delivering data from a data receiver 336, and power from a power receiver 338. It should be appreciated, that although the present invention describes one-way communication from the external circuit to the implant device(s); certain applications may benefit from some form of bi-directional communication, whereas one of ordinary skill in the art can readily adapt the communication circuits depicted to the desired form of bi-directional communication.

Referring to FIG. 13, power and data from the master SoC 332 are shared 344 with the slave SoCs 346a, 346b, through 346n. The master has a global digital circuit 340 and multi-channel (1024) channel stimulator 342 as described in previous sections. The slave SoCs also provide power receiver sections (348a seen in SoC 346a), and data receiver sections (350a seen in SoC 346a), which are inactive, disabled or removed as desired. The slave SoCs have their own GDCs (352a seen in SoC 346a), and multi-channel (1024) stimulators (354a seen in SoC 346a) for controlling stimulators that are not handled by master SoC 332. Each of the SoC devices receives a chip ID, such as the master ID=0, with the other SoCs having IDs of 1 to 3. It should be appreciated that this ID can be set during the packaging process by connecting the ID pin to either ground or $V_{ddL}$, or by alternate means as will be recognized by one of ordinary skill in the art.

Figure 14:
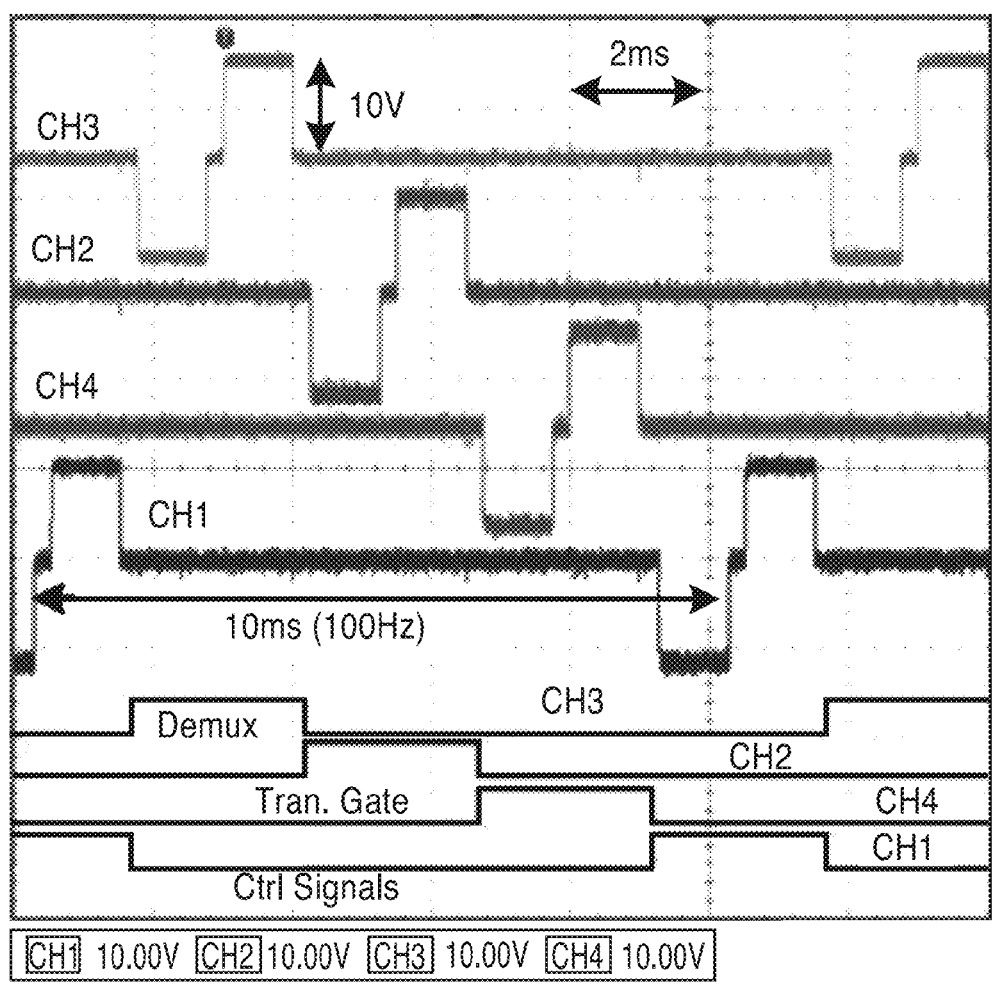
FIG. 14 is a waveform diagram showing output pads being sequentially driven in a high channel count high-voltage stimulator circuit according to an embodiment of the present invention.

FIG. 14 depicts digital timing captured from operation of the clustering device, wherein multiplexed outputs (CH1 through CH4) of a given pixel are seen being sequentially driven by the same current driver through a 1:4 demultiplexor, which was described herein in a previous section. The peaks are seen at 10V for each output, with a period between outputs on each channel as 10 ms. It should be appreciated that 10V is the compliance voltage for the device, while 12V is the supply voltage of the stimulator. There is 2V of headroom in the design, whereby 2V is occupied by the minimum voltage for this stimulator to operate. Signals seen at the bottom of the timing diagram depict demultiplexor transistor gate control signals for channels 1 through 4. The test conditions include a 40 kΩ load per channel with an output current of 250 μA.

Figure 15A:
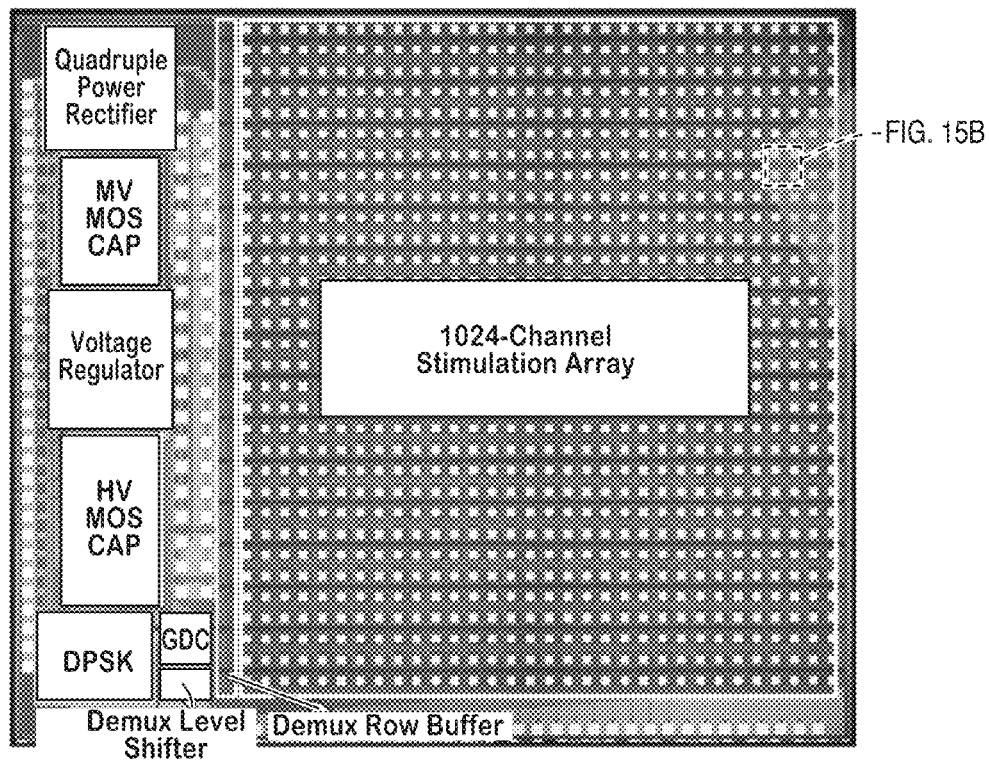
FIG. 15A through FIG. 15C are circuit layout details according to at least one embodiment of the present invention.
Figure 15B:
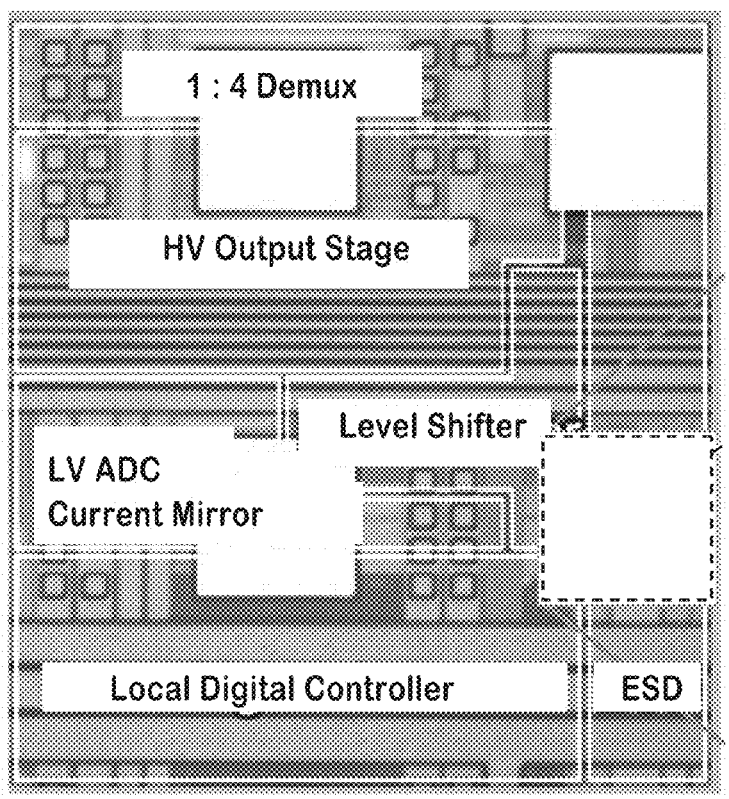
Figure 15C:
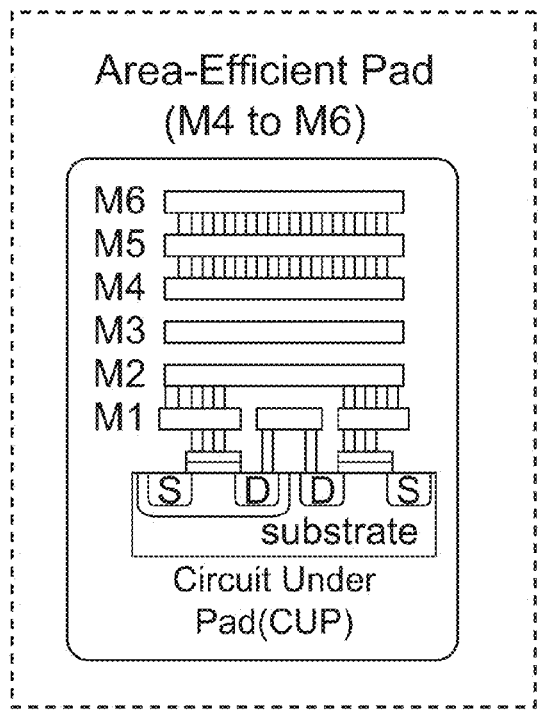

FIG. 15A through FIG. 15C illustrate an example embodiment of a fabricated 1024 channel stimulator array, such as for use in a retinal prosthesis. In FIG. 15A is seen a photograph of the SoC chip with sections marked for: 1024 channel array, quad power rectifier, LV (MV) MOS capacitors, voltage regulator, HV MOS capacitors, DPSK, GDC, demux level shifter and demux row buffer.

In FIG. 15B a close up is seen of a circuit under pad (CUP) construction of the SoC chip fabrication, in which output pads in the pixels are constructed using metal layers M4 to M6, instead of all 6 metal layers, saving the space underneath for active circuits and routing. In FIG. 15C, the metal layers are seen with M4-M6 comprising the pads, with layers underneath utilized for active circuits. These area-efficient pads reduce pixel area significantly, by 22% for example, in this example embodiment. The resultant integrated 1024-channel retinal SoC has an area of 37.6 mm$^2$, requiring only six off-chip capacitors (resonance and storage) and one oscillator for the implant, thus simplifying device packaging.

The quad-level power rectifier delivers 100 mW at a VCE of 83%. The use of non-ideal sample-exclusion scheme (NSE) coupled with programmable threshold voltages enables the DPSK receiver to function at high communication rates, such as 2 Mbps, with a low bit-error-rate (BER) which in the example embodiment was less than $10^{-7}$. The ±10V-compliant pixel array also supports an expansion of 4096 channels using chip clustering. This IC is ready for use in next-generation retinal prostheses.

It should be appreciated that the prosthetic stimulator of the invention can be utilized in a number of stimulator applications. By way of example and not limitation, stimulation of the spinal cord has been shown to have great potential for improving function after motor deficits caused by injury or pathological conditions. Using a wide range of animal models, many studies have shown that stimulation applied to the neural networks intrinsic to the spinal cord can result in a dramatic improvement of motor ability, even allowing an animal to step and stand after a complete spinal cord transection. Clinical use of this technology, however, has been slow to develop due to the invasive nature of the implantation procedures, the lack of versatility in conventional stimulation technology, and the difficulty of ascertaining specific sites of stimulation that would provide optimal amelioration of the motor deficits. Moreover, the development of tools available to control precise stimulation chronically via biocompatible electrodes has been limited.

FIG. 16A through FIG. 16D depict electromyogram (EMG) plots (recordings) for standing and stepping taken at two ankle locations in a laboratory rat. It will be noted that nerves control the muscles in the body utilizing electrical signals called impulses, and that an EMG measures electrical activity of muscles at rest and during contraction.

Figure 16A:
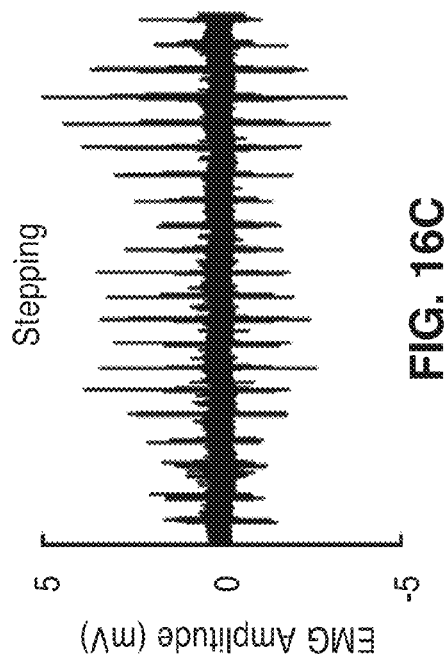
FIG. 16A through FIG. 16D are electromyogram (EMG) waveforms at ankle extensors and flexors for standing and stepping, utilizing a high channel count high-voltage stimulator circuit according to an embodiment of the present invention.
Figure 16C:
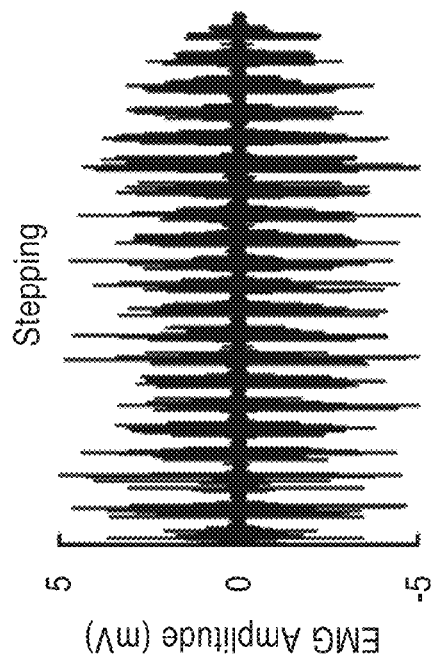
Figure 16B:
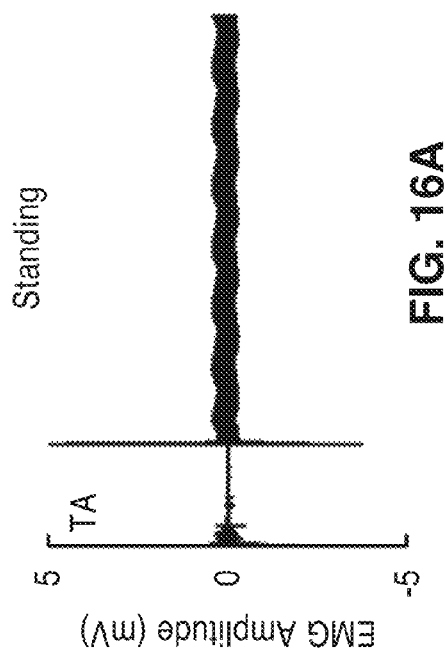
Figure 16D:
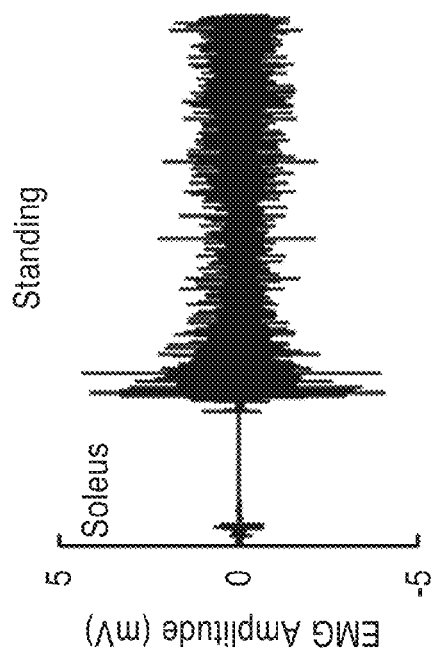

The EMG readings were obtained from the primary ankle flexor (Tibialis Anterior, TA) and ankle extensor (soleus) muscles while suspended with a partial body weight support with their feet on a rodent sized treadmill during partial weight bearing standing and bipedal stepping (treadmill speed 13.5 cm/s) under the influence of epidural stimulation between L2 and S1 at 40 Hz, 375 μA, 0.125 cathodic and anodic pulse width. In particular, FIG. 16A depicts EMG at the TA for standing; FIG. 16B depicts EMG at the soleus for standing; FIG. 16C depicts EMG at the TA for stepping; and FIG. 16D depicts EMG at the soleus for stepping.

The figure represents experiments performed in adult female Sprague dawley rats 12 days post complete spinal cord transection at T8 spinal level resulting in complete paralysis below the waist. Biocompatible electrodes are implanted in ankle flexors (Tibialis Anterior, TA) and ankle extensor (soleus) muscles to record EMG activity. Epidural wires are sutured to the dura of the spinal cord at L2 and S1 spinal levels to stimulate the spinal cord. The animals were suspended using a specially designed body weight support for rodents with their feet placed on a treadmill. All procedures described below are in accordance with the National Institute of Health Guide for the Care and Use of Laboratory Animals and were approved by the Animal Research Committee at UCLA.

Stimulation at 40 Hz (biphasic pulse 0.125 ms anodic and cathodic with 0 interpulse delay, 375 µA) resulted in coordinated activation of the extensor muscles in both hindlimbs leading to partial weight-bearing standing. Thus, distinct motor responses were enabled by stimulation of the spinal epidural electrodes. In this figure there is an initial flexion (increased activation of the TA), followed by a gradual increase in the level of excitation of the extensors.

Using the same configuration of stimulation when the treadmill was turned on, the hindlimbs displayed an alternating robust stepping like movement with partial body weight support characterized by the alternating pattern of EMG between the flexors and extensors.

The above illustrates that the present invention may be utilized in numerous motor restorative applications, such as restoring motor function after a stroke, or relating to Parkinson's disease, or Alzheimer's disease, or providing a cure for foot drop, or similar restoration.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. An apparatus for performing high-voltage high-count neural stimulation for medical implants, comprising: an implant circuit configured for implanting as a medical implant within a patient; an external circuit which is configured for being retained externally to the patient for registering conditions to be processed and communicated as registered conditions to said implant circuit; at least one inductive coupling between said implant circuit and said external circuit over which power and data are communicated from said external circuit to said implant circuit; wherein a transmitter circuit in said external circuit and a receiver circuit in said implant circuit, utilize modulation of a carrier wave to communicate data from said external circuit to said implant circuit; a plurality of stimulator pixels arranged in at least a two dimensional array in said implant circuit, with each stimulator pixel configured with demultiplexing circuitry that demultiplexes data received by the pixel so that multiple neural stimulator outputs are generated using a shared current driver by each of said stimulator pixels; level shifting circuitry within said implant circuitry, said level shifting circuitry is configured for shifting digital signals derived from a low voltage logic supply to high-voltage signals which provides a sufficiently high-voltage for neural stimulation; and wherein said implant circuit is configured to convert registered conditions into stimulation parameters based on sensitivity thresholds for an individual patient, and to generate high-voltage neural stimulation to a high count of neural stimulator outputs.

2. The apparatus of any of the previous embodiments, wherein said implant circuit is further configured with a master-slave selection mechanism and chip clustering circuitry whereby one said implant circuit operates as a master to communicate power and data from said external circuit to itself and one or more implant circuits which operate as slaves thus increasing the number of stimulator outputs supported within said implant and still providing independent control within each said implant circuit within a cluster of interconnected implant circuits.

3. The apparatus of any of the previous embodiments, wherein said chip clustering circuitry is configured for utilizing one master implant circuit coupled to three slave implant circuits within said cluster.

4. The apparatus of any of the previous embodiments, wherein each said implant circuit provides at least one thousand nerve stimulator outputs, whereby said cluster provides at least four thousand nerve stimulator outputs.

5. The apparatus of any of the previous embodiments, wherein said level shifting circuitry within said implant circuit comprises three stage level shifting, wherein a non-differential first voltage is first converted to a differential first voltage, then from a differential first voltage to a partially differential second voltage, then to a fully differential second voltage; wherein said second voltage is a high-voltage, exceeding said first voltage, and at or above approximately plus and minus 10 Volts.

6. The apparatus of any of the previous embodiments, further comprising electrical charge cancellation circuitry within said implant circuit, said electrical charge cancellation circuitry is configured for eliminating residual charge for different sink and source mismatches, different electrodes, and variable stimulation amplitudes.

7. The apparatus of any of the previous embodiments, wherein said implant circuit has an integrated multivoltage on-chip rectifier which eliminates the necessity of off-chip diodes toward simplifying implant circuit packaging.

8. The apparatus of any of the previous embodiments, wherein said implant circuit is configured for fabrication with duplicates of critical I/O pads on the peripheral and center of a fabricated integrated implant circuit toward providing increased adaptability to packaging.

9. The apparatus of any of the previous embodiments, wherein said high count of stimulators comprises multiple hundreds of stimulator outputs.

10. The apparatus of any of the previous embodiments, wherein said high count of stimulators comprises over a thousand stimulator outputs.

11. The apparatus of any of the previous embodiments, wherein said high count of stimulators comprises over four thousand stimulator outputs.

12. The apparatus of any of the previous embodiments, wherein communication utilizing modulation of the carrier wave comprises a form of differential phase shift keying (DPSK).

13. The apparatus of any of the previous embodiments, further comprising two capacitor array circuits in said implant circuit for performing communication by modulated carrier wave; wherein a first capacitor array comprises capacitors and switches for performing non-inverting operations, and a second capacitor array comprises capacitors and switches for performing inverting operations, toward minimizing the number of switching elements required in said implant circuit.

14. The apparatus of any of the previous embodiments, wherein communication by modulation of the carrier wave incorporates a 2nd-order high-pass filter (HPF) to suppress power signal interference, a programmable threshold voltage set to a level for reducing noise interference, and a non-ideal sample-exclusion scheme (NSE) reduces integration noise from phase transition, which reduces bit error rate (BER) of said communication.

15. The apparatus of any of the previous embodiments, wherein said implant circuit further comprises a transistor-based timing-controlled rectifier for efficiently rectifying power communicated from said external circuit to said implant circuit.

16. The apparatus of any of the previous embodiments, wherein said transistor-based timing-controlled rectifier further includes rectification comprising triple well CMOS, having PMOS and NMOS transistors, configured with a high-voltage well (HVNW) to a P– substrate, so that the inherent parasitic bi-polar junction transistor (BJT) is kept off at high input voltages in response to dynamic substrate biasing.

17. The apparatus of any of the previous embodiments, wherein said implant circuit is configured for being fabricated with a circuit-under-pad topology in which active stimulator circuits are fabricated in device layers beneath one or more external pad layers configured for neural connection.

18. The apparatus of any of the previous embodiments, wherein said implant circuit comprises an epiretinal implant circuit configured for receiving image information as said registered condition and generating stimulation outputs configured to connection of optic nerves to render sight to the patient.

19. The apparatus of any of the previous embodiments, wherein said external circuit for said epiretinal implant comprises a camera for registering sequential image information 20. The apparatus of any of the previous embodiments, wherein said apparatus is utilized in an implant selected from a group of nerve stimulator implants consisting of epiretinal, spinal and cochlear.

21. The apparatus of any of the previous embodiments, wherein said apparatus is utilized for restoring motor function to a patient.

22. The apparatus of any of the previous embodiments, wherein restoration of motor function by said apparatus is directed to overcome effects of a stroke, Parkinson's disease, Alzheimer's disease, or foot drop.

23. The apparatus of any of the previous embodiments, wherein said apparatus is utilized for cortex stimulation toward obtaining an increased understanding of brain dynamics.

24. The apparatus of any of the previous embodiments, wherein said apparatus is utilized for cortex stimulation as a treatment for memory loss, epilepsy, Parkinson's disease, and Alzheimer's disease.

25. An apparatus for performing high-voltage high-count neural stimulation for medical implants, comprising: an implant circuit configured for implanting as a medical implant within a patient; an external circuit which is external to the patient and configured for registering conditions to be processed and communicated as registered conditions to said implant circuit; at least one inductive coupling between said implant circuit and said external circuit over which power and data are communicated from said external circuit to said implant circuit; wherein a transmitter circuit in said external circuit and a receiver circuit in said implant circuit, utilize modulation of a carrier wave to communicate data from said external circuit to said implant circuit; a plurality of stimulator pixels arranged in at least a two dimensional array in said implant circuit, with each stimulator pixel configured with demultiplexing circuitry that demultiplexes data received by the pixel so that multiple neural stimulator outputs are generated using a shared current driver by each of said stimulator pixels; level shifting circuitry within said implant circuit, said level shifting circuitry is configured for shifting digital signals derived from a low voltage logic supply to high-voltage signals which provides a sufficiently high-voltage for neural stimulation; and wherein said implant circuit is configured to convert registered conditions into high-voltage neural stimulation to a high count of neural stimulator outputs; wherein said implant circuit is configured with a master-slave selection mechanism and chip clustering circuitry whereby one said implant circuit operates as a master to communicate power and data from said external circuit to itself and one or implant circuits which operate as slaves thus increasing the number of stimulator outputs supported within said implant and still providing independent control within each said implant circuit within a cluster of interconnected implant circuits.

26. A method of generating high-voltage high-count neural stimulation for medical implants, comprising: coupling an implant circuit configured for implanting as a medical implant within a patient with an external circuit, external to the patient, and configured for registering conditions to be processed and communicated as registered conditions to the implant circuit; performing inductive coupling between the implant circuit and the external circuit over which power and data are communicated from the external circuit to the implant circuit; modulating a carrier wave to communicate data between the external circuit and the implant circuit; performing demultiplexing of data received from the carrier wave to drive stimulator channels in the implant circuit, with multiple rows of buffers, each driving multiple pixels which each drive multiple stimulator channels through shared current drivers; performing level shifting within the implant circuit to shift digital signals to high-voltage signals providing a sufficiently high-voltage for neural stimulation; and wherein said implant circuit is configured for converting registered conditions at the external circuit into high-voltage neural stimulation of a high count of neural stimulator outputs.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for performing high-voltage high-count neural stimulation for medical implants, comprising:
    an implant circuit configured for implanting as a medical implant within a patient;
    an external circuit which is configured for being retained externally to the patient for registering conditions to be processed and communicated as registered conditions to said implant circuit;
    at least one inductive coupling between said implant circuit and said external circuit over which power and data are communicated from said external circuit to said implant circuit;
    wherein a transmitter circuit in said external circuit and a receiver circuit in said implant circuit, utilize modulation of a carrier wave to communicate data from said external circuit to said implant circuit;
    a plurality of stimulator pixels arranged in at least a two dimensional array in said implant circuit, with each stimulator pixel configured with demultiplexing circuitry that demultiplexes data received by the pixel so that multiple neural stimulator outputs are generated using a shared current driver by each of said stimulator pixels;
    level shifting circuitry within said implant circuitry, said level shifting circuitry is configured for shifting digital signals derived from a low voltage logic supply to high-voltage signals which provides a sufficiently high-voltage for neural stimulation; and
    wherein said implant circuit is configured to convert registered conditions into stimulation parameters based on sensitivity thresholds for an individual patient, and to generate high-voltage neural stimulation to a high count of neural stimulator outputs.

2. The apparatus recited in claim 1, wherein said implant circuit is further configured with a master-slave selection mechanism and chip clustering circuitry whereby one said implant circuit operates as a master to communicate power and data from said external circuit to itself and one or more implant circuits which operate as slaves thus increasing the number of stimulator outputs supported within said implant and still providing independent control within each said implant circuit within a cluster of interconnected implant circuits.

3. The apparatus recited in claim 2, wherein said chip clustering circuitry is configured for utilizing one master implant circuit coupled to three slave implant circuits within said cluster.

4. The apparatus recited in claim 3, wherein each said implant circuit provides at least one thousand nerve stimulator outputs, whereby said cluster provides at least four thousand nerve stimulator outputs.

5. The apparatus recited in claim 1:
    wherein said level shifting circuitry within said implant circuit comprises three stage level shifting, wherein a non-differential first voltage is first converted to a differential first voltage, then from a differential first voltage to a partially differential second voltage, then to a fully differential second voltage; and
    wherein said second voltage is a high-voltage, exceeding said first voltage, and at or above approximately plus and minus 10 Volts.

6. The apparatus recited in claim 1, further comprising electrical charge cancellation circuitry within said implant circuit, said electrical charge cancellation circuitry is configured for eliminating residual charge for different sink and source mismatches, different electrodes, and variable stimulation amplitudes.

7. The apparatus recited in claim 1, wherein said implant circuit has an integrated multivoltage on-chip rectifier which eliminates the necessity of off-chip diodes toward simplifying implant circuit packaging.

8. The apparatus recited in claim 1, wherein said implant circuit is configured for fabrication with duplicates of critical I/O pads on the peripheral and center of a fabricated integrated implant circuit toward providing increased adaptability to packaging.

9. The apparatus recited in claim 1, wherein said high count of stimulators comprises multiple hundreds of stimulator outputs.

10. The apparatus recited in claim 1, wherein said high count of stimulators comprises over a thousand stimulator outputs.

11. The apparatus recited in claim 1, wherein said high count of stimulators comprises over four thousand stimulator outputs.

12. The apparatus recited in claim 1, wherein communication utilizing modulation of the carrier wave comprises a form of differential phase shift keying (DPSK).

13. The apparatus recited in claim 1:
    further comprising two capacitor array circuits in said implant circuit for performing communication by modulated carrier wave;
    wherein a first capacitor array comprises capacitors and switches for performing non-inverting operations, and a second capacitor array comprises capacitors and switches for performing inverting operations, toward minimizing the number of switching elements required in said implant circuit.

14. The apparatus recited in claim 1, wherein communication by modulation of the carrier wave incorporates a 2nd-order high-pass filter (HPF) to suppress power signal interference, a programmable threshold voltage set to a level for reducing noise interference, and a non-ideal sample-exclusion scheme (NSE) reduces integration noise from phase transition, which reduces bit error rate (BER) of said communication.

15. The apparatus recited in claim 1, wherein said implant circuit further comprises a transistor-based timing-controlled rectifier for efficiently rectifying power communicated from said external circuit to said implant circuit.

16. The apparatus recited in claim 15, wherein said transistor-based timing-controlled rectifier further includes rectification comprising triple well CMOS, having PMOS and NMOS transistors, configured with a high-voltage well (HVNW) to a P− substrate, so that the inherent parasitic bi-polar junction transistor (BJT) is kept off at high input voltages in response to dynamic substrate biasing.

17. The apparatus recited in claim 1, wherein said implant circuit is configured for being fabricated with a circuit-under-pad topology in which active stimulator circuits are fabricated in device layers beneath one or more external pad layers configured for neural connection.

18. The apparatus recited in claim 1, wherein said implant circuit comprises an epiretinal implant circuit configured for receiving image information as said registered condition and generating stimulation outputs configured to connection of optic nerves to render sight to the patient.

19. The apparatus recited in claim 18, wherein said external circuit for said epiretinal implant comprises a camera for registering sequential image information.

20. The apparatus recited in claim 1, wherein said apparatus is utilized in an implant selected from a group of nerve stimulator implants consisting of epiretinal, spinal and cochlear.

21. The apparatus recited in claim 1, wherein said apparatus is utilized for restoring motor function to a patient.

22. The apparatus recited in claim 21, wherein restoration of motor function by said apparatus is directed to overcome effects of a stroke, Parkinson's disease, Alzheimer's disease, or foot drop.

23. The apparatus recited in claim 1, wherein said apparatus is utilized for cortex stimulation toward obtaining an increased understanding of brain dynamics.

24. The apparatus recited in claim 1, wherein said apparatus is utilized for cortex stimulation as a treatment for memory loss, epilepsy, Parkinson's disease, and Alzheimer's disease.

25. An apparatus for performing high-voltage high-count neural stimulation for medical implants, comprising:
　an implant circuit configured for implanting as a medical implant within a patient;
　an external circuit which is external to the patient and configured for registering conditions to be processed and communicated as registered conditions to said implant circuit;
　at least one inductive coupling between said implant circuit and said external circuit over which power and data are communicated from said external circuit to said implant circuit;
　wherein a transmitter circuit in said external circuit and a receiver circuit in said implant circuit, utilize modulation of a carrier wave to communicate data from said external circuit to said implant circuit;
　a plurality of stimulator pixels arranged in at least a two dimensional array in said implant circuit, with each stimulator pixel configured with demultiplexing circuitry that demultiplexes data received by the pixel so that multiple neural stimulator outputs are generated using a shared current driver by each of said stimulator pixels;
　level shifting circuitry within said implant circuit, said level shifting circuitry is configured for shifting digital signals derived from a low voltage logic supply to high-voltage signals which provides a sufficiently high-voltage for neural stimulation;
　wherein said implant circuit is configured to convert registered conditions into high-voltage neural stimulation to a high count of neural stimulator outputs; and
　wherein said implant circuit is configured with a master-slave selection mechanism and chip clustering circuitry whereby one said implant circuit operates as a master to communicate power and data from said external circuit to itself and one or implant circuits which operate as slaves thus increasing the number of stimulator outputs supported within said implant and still providing independent control within each said implant circuit within a cluster of interconnected implant circuits.

26. A method of generating high-voltage high-count neural stimulation for medical implants, comprising:
　coupling an implant circuit configured for implanting as a medical implant within a patient with an external circuit, external to the patient, and configured for registering conditions to be processed and communicated as registered conditions to the implant circuit;
　performing inductive coupling between the implant circuit and the external circuit over which power and data are communicated from the external circuit to the implant circuit;
　modulating a carrier wave to communicate data between the external circuit and the implant circuit;
　performing demultiplexing of data received from the carrier wave to drive stimulator channels in the implant circuit, with multiple rows of buffers, each driving multiple pixels which each drive multiple stimulator channels through shared current drivers;
　performing level shifting within the implant circuit to shift digital signals to high-voltage signals providing a sufficiently high-voltage for neural stimulation; and
　wherein said implant circuit is configured for converting registered conditions at the external circuit into high-voltage neural stimulation of a high count of neural stimulator outputs.

* * * * *